United States Patent
Wei et al.

(10) Patent No.: US 11,452,677 B2
(45) Date of Patent: Sep. 27, 2022

(54) WATER-SOLUBLE PERSONAL CLEANSING PRODUCT, USES, METHODS AND KIT

(71) Applicant: The Procter & Gamble Company, Cincinnati, OH (US)

(72) Inventors: Karl Shiqing Wei, Mason, OH (US); Min Mao, Deerfield Township, OH (US); Susan Adair Griffiths-Brophy, Middletown, OH (US); Jonathan C Pan, Blue Ash, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 16/944,245

(22) Filed: Jul. 31, 2020

(65) Prior Publication Data

US 2021/0030632 A1 Feb. 4, 2021

Related U.S. Application Data

(60) Provisional application No. 62/880,982, filed on Jul. 31, 2019.

(51) Int. Cl.
| | | |
|---|---|---|
| *A61K 8/02* | (2006.01) | |
| *A61K 8/37* | (2006.01) | |
| *A61K 8/44* | (2006.01) | |
| *A61K 8/46* | (2006.01) | |
| *A61K 8/73* | (2006.01) | |
| *A61K 8/92* | (2006.01) | |
| *A61Q 1/14* | (2006.01) | |

(52) U.S. Cl.
CPC ............. *A61K 8/027* (2013.01); *A61K 8/375* (2013.01); *A61K 8/44* (2013.01); *A61K 8/466* (2013.01); *A61K 8/732* (2013.01); *A61K 8/922* (2013.01); *A61Q 1/14* (2013.01); *A61K 2800/33* (2013.01); *A61K 2800/87* (2013.01); *A61K 2800/88* (2013.01)

(58) Field of Classification Search
CPC ........ A61K 8/027; A61K 8/375; A61K 8/732; A61K 8/922; A61K 2800/33
See application file for complete search history.

(56) References Cited

U.S. PATENT DOCUMENTS

| | | | | |
|---|---|---|---|---|
| 5,810,961 | A * | 9/1998 | Andersen | ................. B29C 43/46 156/324 |
| 6,491,931 | B1 * | 12/2002 | Collin | ...................... A61K 8/02 424/401 |
| 6,753,063 | B1 * | 6/2004 | Pung | ..................... A61K 8/0208 15/104.93 |
| 8,197,830 | B2 * | 6/2012 | Helfman | .................. A47L 13/17 424/401 |
| 8,821,687 | B2 | 9/2014 | Muvundamina | |
| 9,545,364 | B2 | 1/2017 | Glenn, Jr. | |
| 9,974,726 | B2 | 5/2018 | Elder | |
| 10,717,839 | B2 | 7/2020 | Mao | |
| 2002/0086039 | A1 | 7/2002 | Lee et al. | |
| 2004/0071755 | A1 | 4/2004 | Fox | |
| 2005/0158369 | A1 * | 7/2005 | Dorschner | ........... C11D 17/049 424/443 |
| 2006/0159729 | A1 * | 7/2006 | Helfman | .................. A47L 13/17 424/443 |
| 2007/0110792 | A9 | 5/2007 | Simon | |
| 2007/0134481 | A1 | 6/2007 | Aubrun-sonneville | |
| 2007/0282520 | A1 | 12/2007 | Cradick | |
| 2008/0035174 | A1 | 2/2008 | Aubrun-sonneville | |
| 2010/0150976 | A1 | 6/2010 | Schnitzler | |
| 2011/0033509 | A1 | 2/2011 | Simon | |
| 2012/0021026 | A1 | 1/2012 | Glenn, Jr. | |
| 2012/0052036 | A1 | 3/2012 | Glenn, Jr. | |
| 2014/0287973 | A1 * | 9/2014 | Sivik | .................... A61K 8/8129 510/119 |
| 2014/0329428 | A1 | 11/2014 | Glenn, Jr. | |

(Continued)

FOREIGN PATENT DOCUMENTS

| | | |
|---|---|---|
| AU | 2011247849 B2 | 12/2012 |
| EP | 1618925 B1 | 9/2007 |

(Continued)

OTHER PUBLICATIONS

"Make-Up Removing Wipes", Mintel GNPD, Feb. 19, 2019.
"Make-Up Removing Wipes", Mintel GNPD, May 13, 2019.
PCT International Search Report and Written Opinion for PCT/US2020/070340 dated Oct. 9, 2020.
"Protelan AGL 95 Acylglutamates the reason of a choice", Zschimmer and Schwarz Italiana S.p.A., Jan. 1, 2004, pp. 1-32.
All Office Actions, U.S. Appl. No. 16/913,116.
STIC Search Report dated Sep. 27, 2021.

*Primary Examiner* — Robert A Wax
*Assistant Examiner* — Olga V. Tcherkasskaya
(74) *Attorney, Agent, or Firm* — Alexandra S. Anoff

(57) ABSTRACT

Described herein, a water-soluble personal cleansing product, its uses, methods and kit, preferably a water-soluble facial cleansing product, comprising a water-soluble fibrous structure; wherein the water-soluble fibrous structure comprises a plurality of fibrous elements; wherein the plurality of fibrous elements comprises: one or more fibrous element-forming materials comprising one or more hydroxyl polymers comprising a natural starch and/or a modified starch; wherein the plurality of fibrous elements is substantially free of surfactant; wherein the water-soluble personal cleansing product comprises one or more surfaces wherein the one or more surfaces are coated with an oily composition, wherein the oily composition comprises one or more oil ingredients. Alternatively, the one or more surfaces are coated with a cleansing composition comprising one or more surfactants; and wherein the cleansing composition is substantially free of alkyl sulfate and alkyl ether sulfate type of surfactants.

22 Claims, No Drawings

(56) References Cited

U.S. PATENT DOCUMENTS

| | | |
|---|---|---|
| 2014/0352711 A1 | 12/2014 | Hoffmann et al. |
| 2015/0315350 A1 | 11/2015 | Mao |
| 2016/0008235 A1* | 1/2016 | Sivik .................. C11D 17/0039 |
| | | 424/401 |
| 2016/0101204 A1* | 4/2016 | Lynch ....................... C11B 9/00 |
| | | 424/443 |
| 2016/0340624 A1* | 11/2016 | Sivik ......................... C11D 1/75 |
| 2016/0374906 A1* | 12/2016 | Sivik .................... A61K 8/8129 |
| | | 424/401 |
| 2017/0282520 A1* | 10/2017 | Cabell ....................... B32B 5/26 |
| 2018/0163325 A1 | 6/2018 | Glenn, Jr. |
| 2018/0258555 A1 | 9/2018 | Glenn, Jr. |
| 2018/0333338 A1 | 11/2018 | Cecola |
| 2019/0083369 A1 | 3/2019 | Dondeyne |
| 2020/0071851 A1 | 3/2020 | Glenn, Jr. |
| 2020/0405605 A1 | 12/2020 | Wei et al. |

FOREIGN PATENT DOCUMENTS

| | | |
|---|---|---|
| WO | 2007093558 A1 | 8/2007 |
| WO | 2012095410 A1 | 7/2012 |
| WO | 2016090514 A1 | 6/2016 |

* cited by examiner

WATER-SOLUBLE PERSONAL CLEANSING PRODUCT, USES, METHODS AND KIT

FIELD OF THE INVENTION

The present application generally relates to water-soluble personal cleansing products, preferably water-soluble facial cleansing products, uses, methods and its kit. The water-soluble personal cleansing product includes a water-soluble fibrous structure. The water-soluble fibrous structure comprises a plurality of fibrous elements; wherein the plurality of fibrous elements comprises: one or more fibrous element-forming materials comprising one or more hydroxyl polymers comprising a natural starch and/or a modified starch. The plurality of fibrous elements is substantially free of surfactant. The water-soluble personal cleansing product comprises one or more surfaces, preferably a top surface and a bottom surface, wherein the one or more surfaces, preferably the top surface, are coated with an oily composition, wherein the oily composition comprises one or more oil ingredients. Alternatively, the one or more surfaces, preferably the top surface, are coated with a cleansing composition comprising one or more surfactants; and wherein the cleansing composition is substantially free of alkyl sulfate and alkyl ether sulfate type of surfactants.

BACKGROUND OF THE INVENTION

The cleansing of the skin, especially the facial skin, the removal of any residues, e.g. make-up, from the skin are very important for the care of keratinous materials (i.e. skin and keratin fibers such as the eyelashes). It shall be most effective to cleanse the fatty residues from the skin, such as the residues of the cosmetic products and the make-up products used daily, in particular from within the skin folds, from the surface of the skin, and from obstruction of the pores of the skin which may cause the appearance of skin impairments.

Current make-up techniques are increasingly innovative and efficient, and more and more make-up product users use long-lasting products such as transfer-resistant foundations, long-lasting lipsticks, waterproof mascaras or double-action mascaras (application of a base and then of the mascara).

However, products of this type are more difficult to remove than standard make-up products, and there is consequently a need for make-up removing products that are not only very efficient and practical to use but are also gentle to the skin and eye areas, while at the same time having good cosmetic qualities (gentle and comfortable to use).

Among the make-up removing products commonly proposed, compositions in liquid form may mainly be found, such as make-up removing oils, which, although efficient, are difficult to remove from the skin because they rinse off poorly, and they are relatively impractical to use since there is a risk of the product running onto the hands. Generally, a residual film remains typically on the skin which is unpleasant for the consumers.

The majority of available make-up remover compositions are typically biphase, i.e. composed of two distinct phases, in particular an aqueous phase and an oily phase, which require prior stirring before application, see for instance US 2019/0083369 A1. Such formulations allow good removability, but leave a finish on the skin that is often bold.

There also exists micellar water compositions, which are compositions of monophase fluids which confer a freshness to the application. Such compositions are however not very effective on a long-lasting make-up.

To palliate to these inconveniences, a combination of sunflower wax and of particular surfactants makes it possible to formulate an oil-based make-up removing composition that is easily rinsable, see WO 2012/095410 A1.

Furthermore, the surfactants used in the aqueous personal cleansing products typically comprise an anionic surfactant, or primary as a detergent of the anionic surfactant and another surfactant selected from the class of one or a plurality of detergent to be blended in combination. The anionic surfactant is, for excellent cleaning and foaming properties, the cleaning agent is often used as a detergent and cleaning products.

Sulfate-based surfactant (for example, sodium lauryl sulfate and sodium lauryl ether sulfate and the like) is, mostly used in personal cleansing compositions. However, the often use of a sulfate-based anionic surfactant of the sulfate-based might be harsh, irritating in terms of dryness to the skin of the face and might induce ocular irritation. Personal or facial cleansing compositions that do not contain any sulfate-based anionic surfactants have been pursued, however with poor cleansing or foaming characteristics.

Numerous compositions for the removal of make-up have already been tested as well as commercialized indicating that until now no solution has been found which satisfies all consumer needs best, especially as far as rather sensitive areas of the skin, e.g. the area around the eye, are concerned. Such compositions or products shall be non-irritant to the mucous membrane of the eye and not cause any discomfort to the user such as a smarting or stinging sensation.

Whereas on the one hand there is the wish to use rather mild and non-irritant lotions for make-up removal on the other hand nowadays water-resistant make-up is becoming more and more popular, however, requiring rather powerful components and applicators for its removal.

An alleged gentle cleansing composition may include: (a) a taurate surfactant; (b) an isethionate surfactant; (c) a betaine (and/or another amphoteric surfactant); and (d) a nonionic emulsifier, see U.S. Pat. No. 9,974,726 B2.

A cosmetic composition for the removal of make-up can be obtained by mixing at least the following ingredients: a) water, b) at least one surfactant, c) at least one emulsion, d) at least one oil or wax component selected from the group consisting of vegetable, animal and mineral oils and waxes, and e) at least one silicon oil and/or wax component, see EP 1 618 925 B1. However, those solutions are not sustainable in a friendly environmental point of view.

In addition, cosmetic compositions that contain a relatively high level of water such as most fluid compositions used on the skin require preservation. This is typically accomplished by using materials that can preserve fluid compositions against various bacteria, fungi and/or yeasts/molds. However, the use of these materials as preservatives may result in skin irritation. Exclusion of such preservative materials would be preferred.

Fibrous structures comprising active agents that provide cleaning are known in the art. However, there is still a need to provide a sustainable personal cleansing product that can clean the skin, especially a facial cleansing product of single use being able to remove make-up from the skin. In that case, preventing ocular irritation might be desirably addressed.

SUMMARY OF THE INVENTION

A water-soluble personal cleansing product, preferably a water-soluble facial cleansing product, is provided and comprises a water-soluble fibrous structure; wherein the water-soluble fibrous structure comprises a plurality of fibrous elements; wherein the plurality of fibrous elements comprises: one or more fibrous element-forming materials comprising one or more hydroxyl polymers comprising a natural starch and/or a modified starch; wherein the plurality of fibrous elements is substantially free of surfactant; wherein the water-soluble personal cleansing product comprises one or more surfaces, preferably a top surface and a bottom surface, wherein the one or more surfaces, preferably the top surface, are coated with an oily composition, wherein the oily composition comprises one or more oil ingredients.

Alternatively, a water-soluble personal cleansing product, preferably a water-soluble facial cleansing product, is provided and comprises a water-soluble fibrous structure; wherein the water-soluble fibrous structure comprises a plurality of fibrous elements; wherein the plurality of fibrous elements comprises: one or more fibrous element-forming materials comprising one or more hydroxyl polymers comprising a natural starch and/or a modified starch; wherein the plurality of fibrous elements is substantially free of surfactant; wherein the water-soluble personal cleansing product comprises one or more surfaces, preferably a top surface and a bottom surface, wherein the one or more surfaces, preferably the top surface, are coated with a cleansing composition comprising one or more surfactants; and wherein the cleansing composition is substantially free of alkyl sulfate and alkyl ether sulfate type of surfactants.

Use of the water-soluble personal cleansing product as set out hereinbefore for make-up removal from the skin, preferably for eye make-up removal.

A kit for make-up removal from the skin, preferably for eye make-up removal, is provided and comprises:
i) a first water-soluble personal cleansing product comprising the water-soluble personal cleansing product as set out hereinbefore; and
ii) a second water-soluble personal cleansing product, preferably a second water-soluble facial cleansing product comprising a water-soluble fibrous structure of the second water-soluble personal cleansing product; wherein the water-soluble fibrous structure comprises a plurality of fibrous elements; wherein the plurality of fibrous elements comprises: one or more fibrous element-forming materials comprising one or more polyvinyl alcohol; and one or more active agents present within the plurality of fibrous elements, wherein the one or more active agents comprise one or more surfactants, wherein the one or more surfactants comprise at least one glutamate surfactant according to the general formula (I):

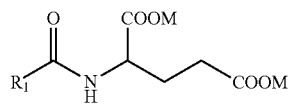

(I)

wherein $R_1$ is a saturated or unsaturated, straight or branched alkyl or alkenyl chain with from 5 to 20 carbon atoms, preferably with from 7 to 17 carbon atoms, more preferably with from 9 to 13 carbon atoms; and M is H, ammonium, triethanolammonium (TEA), sodium or potassium and mixtures thereof; and wherein the water-soluble fibrous structure of the second water-soluble personal cleansing product is substantially free of alkyl sulfate and alkyl ether sulfate type of surfactants.

A method for make-up removal from the skin, preferably for eye make-up removal, is provided and comprises the following steps, preferably in that order:
a) providing the water-soluble personal cleansing product as defined hereinbefore;
b) removing any make-up residues from the skin by applying the one or more surfaces, preferably the top surface, of the water-soluble personal cleansing product comprising the oily composition; optionally rinsing with water.

A method of making a water-soluble personal cleansing product comprising a water-soluble fibrous structure as defined hereinbefore comprising the following steps, preferably in that order:
a) providing a fibrous element-forming composition, wherein the fibrous element-forming composition is an aqueous composition comprising one or more fibrous element-forming materials; and
b) spinning the fibrous element-forming composition into a plurality of fibrous elements forming a water-soluble fibrous structure comprising a plurality of fibrous elements, preferably a plurality of filament elements.

DETAILED DESCRIPTION OF THE INVENTION

Definitions of Terms

In this document, including in all embodiments of all aspects of the present invention, the following definitions apply unless specifically stated otherwise.

All percentages are by weight (w/w) of the respective fibrous element-forming composition, or water-soluble fibrous structure, or water-soluble personal cleansing product, unless otherwise specified. All ratios or percentages are weight ratios or weight percentages unless specifically stated otherwise. "% wt." means percentage by weight. References to "parts" e.g. a mixture of 1 part X and 3 parts Y, is a ratio by weight.

"QSP" or "q.s." means sufficient quantity for 100% or for 100 g. "+/−" indicates the standard deviation. All ranges are inclusive and combinable. The number of significant digits conveys neither a limitation on the indicated amount nor on the accuracy of the measurement.

All measurements are understood to be made under ambient conditions, where "ambient conditions" means at 20° C. at 1 atmosphere (atm) of pressure and at 65% relative humidity, unless otherwise stated. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International.

Herein "min" means "minute" or "minutes". Herein "mol" means mole. Herein "g" following a number means "gram" or "grams". "Ex." means "example". All amounts as they pertain to listed ingredients are based on the active level ("solids") and do not include carriers or by-products that may be included in commercially available materials.

Herein, "comprising" means that other steps and other ingredients can be included in addition. "Comprising" encompasses the terms "consisting of" and "consisting essentially of". The compositions, methods, and uses of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated.

The terms "include," "includes," and "including," as used herein are meant to be non-limiting.

Where amount ranges are given, these are to be understood as being the total amount of said ingredient in the composition or the fibrous structure or the personal cleansing product, or where more than one species fall within the scope of the ingredient definition, the total amount of all ingredients fitting that definition, in the composition, the fibrous structure or the personal cleansing product.

For example, if the composition or the fibrous structure or the personal cleansing product comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the composition or the fibrous structure or the personal cleansing product.

The term "fibrous structure" as used herein means a structure that comprises one or more fibrous elements, optionally with one or more particles. A fibrous structure may mean an association of fibrous elements and particles that together form a fibrous structure, such as a unitary structure, capable of performing a function.

The fibrous structures may be homogeneous or may be layered. If layered, the water-soluble fibrous structures may comprise at least two layers, or at least three layers/or at least four layers or at least five layers.

The fibrous structure may be a multi-ply fibrous structure that exhibits a basis weight of less than 5000 g/m$^2$ as measured according to the Basis Weight Test Method described herein.

The fibrous structure may be a "unitary fibrous structure". The term "unitary fibrous structure" as used herein is an arrangement comprising one or more particles and a plurality of two or more and/or three or more fibrous elements that are inter-entangled or otherwise associated with one another to form a fibrous structure. A unitary fibrous structure may be one or more plies within a multi-ply fibrous structure.

A unitary fibrous structure may comprise three or more different fibrous elements. A unitary fibrous structure may comprise two different fibrous elements, for example a co-formed fibrous structure, upon which a different fibrous element is deposited to form a fibrous structure comprising three or more different fibrous elements.

The term "fibrous element" as used herein means an elongate particulate having a length greatly exceeding its average diameter, i.e. a length to average diameter ratio of at least about 10. A fibrous element may be a filament or a fiber. The fibrous element may be a single fibrous element rather than a yarn comprising a plurality of fibrous elements.

The fibrous elements may be spun from a fibrous element-forming composition via suitable spinning process operations, such as meltblowing, spunbonding, electro-spinning, and/or rotary spinning.

The fibrous elements may be monocomponent and/or multicomponent. For example, the fibrous elements may comprise bicomponent fibers and/or filaments. The bicomponent fibers and/or filaments may be in any form, such as side-by-side, core and sheath, islands-in-the-sea and the like.

The term "filament" as used herein means an elongate particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers. Non-limiting examples of filaments include meltblown and/or spunbond filaments. Non-limiting examples of polymers that can be spun into filaments typically include natural polymers, such as starch, starch derivatives, cellulose, such as rayon and/or lyocell, and cellulose derivatives, hemicellulose, hemicellulose derivatives, and synthetic polymers including, but not limited to thermoplastic polymer filaments, such as polyesters, nylons, polyolefins such as polypropylene filaments, polyethylene filaments, and biodegradable thermoplastic fibers such as polylactic acid filaments, polyhydroxyalkanoate filaments, polyesteramide filaments and polycaprolactone filaments.

The term "fiber" as used herein means an elongate particulate as described above that exhibits a length of less than 5.08 cm (2 in.) and/or less than 3.81 cm (1.5 in.) and/or less than 2.54 cm (1 in.).

Fibers are typically considered discontinuous in nature. Non-limiting examples of fibers include staple fibers produced by spinning a filament or filament tow and then cutting the filament or filament tow into segments of less than 5.08 cm (2 in.) thus producing fibers.

One or more fibers may be formed from a filament, such as when the filaments are cut to shorter lengths (such as less than 5.08 cm in length). Thus, a fiber of the fibrous element may be made from a filament, such as a fiber comprising one or more fibrous element-forming materials. Therefore, references to filament and/or herein also include fibers made from such filament and/or filaments unless otherwise noted. Fibers are typically considered discontinuous in nature relative to filaments, which are considered continuous in nature.

The term "fibrous element-forming composition" as used herein means a composition that is suitable for making a plurality of fibrous elements such as by meltblowing and/or spunbonding. The fibrous element-forming composition comprises one or more fibrous element-forming materials that exhibit properties that make them suitable for spinning into a plurality of fibrous elements.

The term "fibrous element-forming material" as used herein means a material, such as a polymer or monomers capable of producing a polymer that exhibits properties suitable for making a plurality of fibrous elements. The one or more fibrous element-forming materials comprise one or more hydroxyl polymers comprising a natural starch and/or a modified starch.

The term "particle" as used herein means a solid additive, such as a powder, granule, agglomerate, encapsulate, microcapsule, and/or prill. The shape of the particle can be in the form of spheres, rods, plates, tubes, squares, rectangles, discs, stars, fibers or have regular or irregular random forms. The particles, at least those of at least about 44 μm, can be measured by the Particle Size Distribution Test Method described herein. For particles that are less than about 44 μm, a different test method may be used, for example light scattering, to determine the particle sizes less than about 44 μm, for example perfume microcapsules that typically range from about 15 μm to about 44 μm and/or about 25 μm in size.

The water-soluble fibrous structure may comprise a plurality of fibrous elements at a basis weight of from about 1 g/m$^2$ to about 3000 g/m$^2$, preferably from about 10 g/m$^2$ to about 5000 g/m$^2$, more preferably about 20 g/m$^2$ to about 2000 g/m$^2$, even more preferably from about 30 g/m$^2$ to about 1000 g/m², most preferably from about 30 g/m² to about 300 g/m², even most preferably from about 40 g/m² to about 100 g/m² as measured by the Basis Weight Test Method described herein. In one example, the water-soluble fibrous structure comprises two or more layers wherein filaments are present in at least one of the layers at a basis weight of from about 1 g/m² to about 500 g/m².

The solid additives may exhibit a D50 particle size of from about 100 μm to about 5000 μm, preferably from about 100 μm to about 2000 μm, more preferably from about 250 μm to about 1200 μm, even more preferably from about 250 μm to about 850 μm as measured according to the Particle Size Distribution Test Method described herein.

The term "additive" as used herein means any material present that may be in the fibrous element that is not a fibrous element-forming material.

The term "active agent" as used herein means an additive being one or more surfactants, preferably comprising at least a glutamate surfactant as set out hereinafter that produces an intended effect in an environment external to a plurality of fibrous elements and/or a particle and/or a water-soluble fibrous structure comprising a plurality of fibrous elements, such as when the plurality of fibrous elements, and/or the water-soluble fibrous structure is exposed to conditions of intended use.

The term "polysaccharides" as used herein means natural polysaccharides and polysaccharide derivatives and/or modified polysaccharides. Suitable polysaccharides include, but are not limited to, starches, starch derivatives, starch copolymers, chitosan, chitosan derivatives, chitosan copolymers, cellulose, cellulose derivatives, cellulose copolymers, hemicellulose, hemicellulose derivatives, hemicelluloses copolymers, gums, arabinans, galactans, and mixtures thereof. The polysaccharide may exhibit a weight average molecular weight of from about 10,000 g/mol to about 40,000,000 g/mol, preferably from about 100,000 g/mol to about 40,000,000 g/mol, more preferably from about 1,000,000 g/mol to about 40,000,000 g/mol, even more preferably from about 3,000,000 g/mol to about 40,000,000 g/mol.

The polysaccharides may comprise non-cellulose and/or non-cellulose derivative and/or non-cellulose copolymer hydroxyl polymers. Non-limiting example of such non-cellulose polysaccharides may be selected from the group consisting of: starches, starch derivatives, starch copolymers, chitosan, chitosan derivatives, chitosan copolymers, hemicellulose, hemicellulose derivatives, hemicelluloses copolymers, and mixtures thereof.

The term "starch" as used herein includes any naturally occurring unmodified starches, modified starches, synthetic starches and mixtures thereof, as well as mixtures of the amylose or amylopectin fractions; the starch may be modified by physical, chemical, or biological processes, or combinations thereof. The choice of unmodified or modified starch may depend on the end product desired.

The term "conditions of intended use" as used herein means the temperature, physical, chemical, and/or mechanical conditions that a fibrous element and/or particle and/or water-soluble fibrous structure is exposed to when the fibrous element and/or particle and/or water-soluble fibrous structure is used for one or more of its designed purposes. For example, if a fibrous element and/or a particle and/or a water-soluble fibrous structure comprising a fibrous element is designed to be used by a human as a personal cleansing product for the skin, preferably the facial skin care purposes, the conditions of intended use will include those temperature, chemical, physical and/or mechanical conditions present during the cleansing of the human's skin.

The term "weight ratio" as used herein means the ratio between two materials on their dry basis. For example, the weight ratio of fibrous element-forming materials to active agents within a fibrous element is the ratio of the weight of fibrous element-forming material on a dry weight basis (g or %) in the fibrous element to the weight of one or more active agent(s) on a dry weight basis (g or %—same units as the fibrous element-forming material weight) in the fibrous element.

The term "water-soluble material" as used herein means a material that is miscible in water. In other words, a material that is capable of forming a stable (does not separate for greater than 5 minutes after forming the homogeneous solution) homogeneous solution with water at ambient conditions.

The term "ambient conditions" as used herein means 23° C.±1.0° C. and a relative humidity of 50%±2%.

The term "free of" as used herein means that the composition, or the fibrous structure, or the personal cleansing product comprises 0% of an ingredient by total weight of the composition, or by total weight of the fibrous structure, or by total weight of the personal cleansing product, thus no detectable amount of the stated ingredient.

The term "substantially free of" as used herein means less than 1%, less than 0.8%, less than 0.5%, less than 0.3%, or less than an immaterial amount of a stated ingredient by total weight of the composition, or by total weight of the fibrous structure, or by total weight of the personal cleansing product.

The term "mixtures" as used herein is meant to include a simple combination of materials and any compounds that may result from their combination.

The term "weight average molecular weight" as used herein means the weight average molecular weight as determined using gel permeation chromatography according to the protocol found in Colloids and Surfaces A. Physico Chemical & Engineering Aspects, Vol. 162, 2000, pg. 107-121.

The term "length" as used herein, with respect to a fibrous element, means the length along the longest axis of the fibrous element from one terminus to the other terminus. If a fibrous element has a kink, curl or curves in it, then the length is the length along the entire path of the fibrous element from one terminus to the other terminus.

The term "diameter" as used herein, with respect to a fibrous element, is measured according to the Diameter Test Method described herein. A fibrous element may exhibit a diameter of less than about 100 μm and/or less than about 75 μm and/or less than about 50 μm and/or less than about 25 μm and/or less than about 20 μm and/or less than about 15 μm and/or less than about 10 μm and/or less than about 6 μm and/or greater than about 1 μm and/or greater than about 3 μm.

The term "by weight on a dry fibrous element basis" and/or "by weight on a dry particle basis" and/or "by weight on a dry fibrous structure basis" means the weight of the fibrous element and/or particle and/or fibrous structure, respectively, measured immediately after the fibrous element and/or particle and/or fibrous structure, respectively, has been conditioned in a conditioned room at a temperature of 23° C.±1.0° C. and a relative humidity of 50%±10% for 2 hours. By weight on a dry fibrous element basis and/or dry particle basis and/or dry fibrous structure basis may mean that the fibrous element and/or particle and/or fibrous structure comprises less than about 20% and/or less than about 15% and/or less than about 10% and/or less than about 7% and/or less than about 5% and/or less than about 3% and/or to 0% and/or to greater than 0% based on the dry weight of the fibrous element and/or particle and/or water-soluble fibrous structure of moisture, such as water, for example free water, as measured according to the Water Content Test Method described herein.

The term "total level" as used herein, for example with respect to the total level of one or more ingredients present in the fibrous element and/or particle and/or fibrous structure, means the sum of the weights or weight percent of all of the subject materials, for example ingredients.

The objects of the present invention are to provide water-soluble personal cleansing products, water-soluble fibrous structures and uses of the products, the structures and the respective compositions as described in the Summary or as described hereinbelow for fulfilling the technical effects or goals as set out herein. These objects and other advantages as may be apparent to those skilled in the art can be achieved through the present invention, which is described in the above Summary of the Invention and Detailed Description of the invention and which is defined in the claims which follow.

Benefits

Without being bound by theory, the inventors of the present invention have surprisingly found a fibrous structure that is readily water-soluble and essentially comprises materials that are compatible with a desire to provide a sustainable personal cleansing product in a friendly environmental point of view. The water-soluble fibrous structure comprises a plurality of fibrous elements. The plurality of fibrous elements comprises one or more fibrous element-forming materials that can render the personal cleansing product water-soluble and sustainable.

The water-soluble fibrous structure is substantially free, preferably free of any surfactant. The plurality of fibrous elements is substantially free of surfactant.

The water-soluble personal cleansing product can be coated with an oily composition comprising one or more oil ingredients. Oil ingredients have been found to be able to remove make-up residues, especially long-lasting make-up products such as waterproof mascaras or double-action mascaras.

Alternatively, the water-soluble personal cleansing product can be coated with a cleansing composition comprising one or more surfactants, wherein the cleansing composition is substantially free of alkyl sulfate and alkyl ether sulfate type of surfactants.

Both water-soluble personal cleansing products can help for removing make-up products in an efficient, practical and gentle way to the skin and eye areas, while at the same time having good cosmetic qualities (gentle and comfortable to use).

Among the make-up removing products commonly proposed, compositions in liquid form may mainly be found, such as make-up removing oils, which, although efficient, are difficult to remove from the skin because they rinse off poorly, and they are relatively impractical to use since there is a risk of the product running onto the hands. Generally, a residual film remains typically on the skin which is unpleasant for the consumers.

The resulting personal cleansing product can be used for cleaning the skin, especially the facial skin, and is readily water-soluble. Because of the use of oily composition or the surfactants being substantially free of alkyl sulfate and alkyl ether sulfate type of surfactants, when cleaning the ocular region of the facial skin, ocular irritation has been prevented.

The resulting personal cleansing product comprising the fibrous structure does not require any amount of water such that the water-soluble personal cleansing product may be free of any preservatives.

Also, the inventors have found that the water-soluble personal cleansing product can be used with a second water-soluble personal cleansing product supplied in a kit. The second water-soluble personal cleansing product as detailed more below comprises one or more fibrous element-forming materials comprising one or more polyvinyl alcohol; and one or more active agents present within the plurality of fibrous elements, wherein the one or more active agents comprise one or more surfactants, wherein the one or more surfactants comprise at least one glutamate surfactant. Such kit and method of using it can provide a dual benefit, namely the removal of any make-up residues from the skin and cleaning of the skin if any oily residues from the make-up residues remains, while being mild to the skin, and thus preventing any ocular irritation.

When one or more active agents comprising one or more surfactants are present within the plurality of fibrous elements, it is not intended to mean that one or more surfaces of the water-soluble personal cleansing product is coated by the one or more active agents.

Disclaimer

The water-soluble fibrous structure is substantially free, preferably free of surfactant. The water-soluble fibrous structure is substantially free, preferably free of alkyl sulfate and alkyl ether sulfate type of surfactant. Preferably, the water-soluble fibrous structure does not comprise any alkyl sulfate which comprises $C_{12}$-$C_{15}$ alkyl sulfate or any alkyl ether sulfate including alkyl glyceryl ether sulfates.

The water-soluble fibrous structure may not comprise any alkyl ether sulfates which are those having the formula:

$$RO(CH_2CH_2O)_nSO_3M$$

wherein R is an alkyl or alkenyl having 8 to 18 carbons, preferably 12 to 18 carbons, n has an average value of greater than at least 0.5, preferably between 2 and 3; and M is a solubilizing cation such as sodium, potassium, ammonium or substituted ammonium.

The water-soluble fibrous structure may not comprise any ammonium and sodium lauryl ether sulfates.

If the water-soluble fibrous structure does contain alkyl sulfate and/or alkyl ether sulfate type of surfactant, its content of such a weight proportion of: alkyl sulfates or alkyl ether sulfate type surfactant is less than or equal to the sum of 0.6, more preferably less than or equal to the sum of 0.2, even more preferably equal to 0.

Also, the water-soluble personal cleansing product may be substantially free of alkyl sulfate and alkyl ether sulfate type of surfactant, as described hereinbefore.

The water-soluble personal cleansing product comprises a water-soluble fibrous structure comprising a plurality of fibrous elements. The plurality of fibrous elements is substantially free of surfactant, preferably free of surfactant. A surfactant may be an anionic, nonionic, amphoteric, zwitterionic and/or cationic surfactant.

In other words, the plurality of fibrous elements comprises one or more fibrous element-forming materials that are substantially free of surfactant, preferably free of surfactant. The water-soluble fibrous structures, and the plurality of fibrous elements do not comprise any active agents comprising one or more surfactants, present within the plurality of fibrous elements, unless otherwise specified.

Water-Soluble Personal Cleansing Product

A water-soluble personal cleansing product, preferably a water-soluble facial cleansing product is provided and comprises a water-soluble fibrous structure. The water-soluble fibrous structure comprises a plurality of fibrous elements. The water-soluble fibrous structure will be described in more details below.

The water-soluble personal cleansing product may in the form of a wipe, a pad, a facial cleansing wipe or facial cleansing pad for an adult or a baby, a bath tissue wipe, or a skin care substrate. The water-soluble personal cleansing product, preferably the facial cleansing wipe or pad may be used for make-up removal from the skin, especially for eye make-up removal.

Water-Soluble Fibrous Structure

A water-soluble fibrous structure for personal cleansing, preferably for facial cleansing, comprises a plurality of fibrous elements. The plurality of fibrous elements may comprise one or more filaments and/or one or more fibers.

The water-soluble fibrous structure may comprise a plurality of filaments, and one or more particles, preferably wherein the one or more particles comprise one or more active agent-containing particles, such as water-soluble active agent-containing particles.

Even though the plurality of fibrous elements and/or the water-soluble fibrous structure are in solid form, the fibrous element-forming composition used to make the plurality of fibrous elements of the water-soluble fibrous structure may be in the form of a liquid.

The water-soluble fibrous structure comprises a plurality of fibrous elements. The plurality of fibrous elements may be typically identical or substantially identical from a compositional perspective.

Alternatively, the water-soluble fibrous structure may comprise two or more different fibrous elements. Non-limiting examples of differences in the plurality of fibrous elements may be physical differences such as differences in diameter, length, texture, shape, rigidity, elasticity, and the like; chemical differences such as crosslinking level, solubility, melting point, Tg, active agent, fibrous element-forming material, color, level of active agent, basis weight, density, level of fibrous element-forming material, presence of any coating on the plurality of fibrous elements, biodegradable or not, hydrophobic or not, contact angle, and the like; differences in whether the plurality of fibrous elements lose its physical structure when the plurality of fibrous elements and/or particle is exposed to conditions of intended use; differences in whether the fibrous element's morphology changes when the fibrous element is exposed to conditions of intended use; and differences in rate at which the fibrous element releases one or more of its active agents when the fibrous element is exposed to conditions of intended use.

The water-soluble fibrous structure may exhibit different regions, such as different regions of basis weight, density and/or caliper. The water-soluble fibrous structure may comprise texture on one or more of its surfaces. A surface of the water-soluble fibrous structure may comprise a pattern, such as a non-random, repeating pattern. The water-soluble fibrous structure may be embossed with an emboss pattern. The water-soluble fibrous structure may comprise apertures. The apertures may be arranged in a non-random, repeating pattern.

The water-soluble fibrous structure may comprise one or more apertures and thus may be an apertured water-soluble fibrous structure. The water-soluble fibrous structure may comprise a plurality of apertures. The apertures may be arranged in a pattern, for example a repeating pattern, such as a non-random, repeating pattern, and/or a non-repeating pattern.

Apertures within the apertured water-soluble fibrous structure may be of virtually any shape and size. The apertures within the apertured water-soluble fibrous structures may be generally round or oblong shaped, in a regular pattern of spaced apart openings. The water-soluble fibrous structure may comprise two or more apertures that are spaced apart from one another at a distance of from about 0.2 mm to about 100 mm and/or from about 0.5 mm to about 10 mm.

Aperturing of water-soluble fibrous structures may be accomplished by any number of techniques. For example, aperturing can be accomplished by various processes involving bonding and stretching, such as those described in U.S. Pat. Nos. 3,949,127 and 5,873,868.

The apertures may be formed by forming a plurality of spaced, melt stabilized regions, and then ring-rolling the web to stretch the web and form apertures in the melt stabilized regions, as described in U.S. Pat. Nos. 5,628,097 and 5,916,661, both of which are hereby incorporated by reference herein.

Apertures may be formed in a multilayer, water-soluble fibrous structure configuration by the method described in U.S. Pat. Nos. 6,830,800 and 6,863,960 which are hereby incorporated herein by reference. Still another process for aperturing webs is described in U.S. Pat. No. 8,241,543 entitled "Method and Apparatus for Making an Apertured Web", which is hereby incorporated herein by reference. Non-limiting examples of processes for imparting apertures to a water-soluble fibrous structure may include embossing, rodding, rotary knife aperturing, pinning, die cutting, die punching, needle-punching, knurling, crush cutting, shear cutting, pneumatic forming, hydraulic forming, laser cutting, and tufting.

The water-soluble fibrous structure may comprise pinning-imparted apertures. The water-soluble fibrous structure may comprise rodding-imparted apertures. The water-soluble fibrous structure may comprise rotary knife aperturing-imparted apertures The water-soluble fibrous structure may comprise apertures that have been imparted to the water-soluble fibrous structure by different types of aperturing processes.

Apertures may be imparted to a water-soluble fibrous structure during forming of the water-soluble fibrous structure on a collection device, such as a patterned belt, that has features, for example depressions and/or protrusions that impart apertures to the water-soluble fibrous structure upon the fibrous elements contacting the collection device during formation.

The water-soluble fibrous structure may comprise discrete regions of fibrous elements that differ from other parts of the water-soluble fibrous structure.

Non-limiting examples of use of the water-soluble fibrous structure may include, but are not limited to a wipe, a pad, a facial cleansing wipe or facial cleansing pad for an adult or a baby, a bath tissue wipe, or a skin care substrate. The water-soluble fibrous structure may be used for personal cleansing, preferably for facial cleansing, more preferably for make-up removal from the skin, most preferably for eye make-up removal.

The water-soluble fibrous structure may have a basis weight of from about 1 g/m$^2$ to about 3000 g/m$^2$, preferably from about 10 g/m$^2$ to about 5000 g/m$^2$, more preferably about 20 g/m$^2$ to about 2000 g/m$^2$, even more preferably from about 30 g/m$^2$ to about 1000 g/m$^2$, most preferably from about 30 g/m² to about 300 g/m², even most preferably from about 40 g/m² to about 100 g/m² as measured by the Basis Weight Test Method described herein.

The water-soluble fibrous structure may comprise two or more layers wherein filaments are present in at least one of the layers at a basis weight of from about 1 g/m² to about 500 g/m².

Alternatively, the water-soluble personal cleansing product may be a composite comprising a first, second and third layers. The water-soluble fibrous structure may define a first layer which is inserted between a second and third layers. The first layer comprising the water-soluble fibrous structure may have a basis weight of from about 1 g/m² to about 500 g/m², preferably a basis weight of from about 60 g/m² to about 200 g/m², more preferably a basis weight of from about 70 g/m² to about 150 g/m². Each of the second and third layers may have a basis weight of from about 1 g/m² to about 50 g/m², preferably a basis weight of from about 5 g/m² to about 45 g/m², more preferably a basis weight of from about 10 g/m² to about 40 g/m². The water-soluble fibrous structure may be defined as hereinafter. Each of the second and third layers may comprise a plurality of fibrous elements comprising one or more fibrous element-forming materials which includes one or more polyvinyl alcohols.

The one or more fibrous-element forming materials of either or both second and third layers may preferably further comprise two or more polyvinyl alcohols. In that case, one of the two or more polyvinyl alcohols may exhibit a weight average molecular weight of from about 10,000 g/mol to about 100,000 g/mol, preferably from about 20,000 g/mol to about 50,000 g/mol, more preferably from about 25,000 g/mol to about 45,000 g/mol, and the other of two or more polyvinyl alcohols may exhibit a weight average molecular weight of from about 105,000 g/mol to about 40,000,000 g/mol, preferably from about 110,000 g/mol to about 20,000,000 g/mol, more preferably from about 120,000 g/mol to about 500,000 g/mol.

In that case, the oily composition or the cleansing composition as defined hereinafter may be coated on the one or more surfaces of the water-soluble personal cleansing product. The one or more surfaces of the water-soluble personal cleansing product may be defined by either one or both of the second and third layers. A top surface of the water-soluble personal cleansing product may be defined by a top surface of the second layer. A bottom surface of the water-soluble personal cleansing product may be defined by a bottom surface of the third layer.

Fibrous Elements

The water-soluble fibrous structure comprises a plurality of fibrous elements. The plurality of fibrous elements comprises one or more fibrous element-forming materials. The plurality of fibrous elements comprises water-soluble fibrous elements. The plurality of fibrous elements may comprise one or more filaments and/or one or more fibers.

The total level of the one or more fibrous element-forming materials present in the fibrous element may be from about 5% to about 80% by weight on a dry fibrous element basis and/or dry water-soluble fibrous structure basis, preferably from about 10% to about 75% by weight on a dry fibrous element basis and/or dry water-soluble fibrous structure basis, more preferably from about 30% to about 70% by weight on a dry fibrous element basis and/or dry water-soluble fibrous structure basis.

The plurality of fibrous elements comprises one or more fibrous element-forming materials. The one or more fibrous element-forming materials comprises one or more hydroxyl polymers comprising a natural starch and/or a modified starch. In addition, the one or more fibrous element-forming materials may comprise one or more polymers selected from the group consisting of polyacrylamide, carboxyl modified polyacrylamide, polyacrylic acid, poly(hydroxyethyl acrylic acid), polymethacrylic acid and partial esters, polyvinyl alcohol, carboxymethyl cellulose, hydroxypropylmethyl cellulose, polyvinylpyrrolidone, polyamide, polyethylene oxide, and mixtures thereof.

The plurality of fibrous elements may further comprise a plasticizer, such as glycerin and/or sorbitol; and/or pH adjusting agents, such as citric acid.

The plurality fibrous elements may be meltblown and/or spunbond fibrous elements.

The plurality of fibrous elements may be hydrophilic or hydrophobic. The plurality of fibrous elements may be surface treated and/or internally treated to change the inherent hydrophilic or hydrophobic properties of the plurality of fibrous elements.

The plurality of fibrous elements may exhibit a diameter of less than about 100 μm and/or less than about 75 μm and/or less than about 50 μm and/or less than about 25 μm and/or less than about 10 μm and/or less than about 5 μm and/or less than about 1 μm as measured according to the Diameter Test Method described herein.

The plurality of fibrous elements may exhibit a diameter of greater than about 0.5 μm as measured according to the Diameter Test Method described herein.

The plurality of fibrous elements is substantially free of surfactant, preferably free of surfactant, i.e. an anionic, nonionic, amphoteric, zwitterionic and/or cationic surfactant.

Fibrous Element-Forming Material

The water-soluble fibrous structure comprises a plurality of fibrous elements. The plurality of fibrous elements comprises one or more fibrous-element forming materials.

The one or more fibrous-element forming materials can be a polymer or monomers capable of producing a polymer that exhibits properties suitable for making a fibrous element, e.g. a filament, such as by a spinning or spunbonding or meltblowing process.

The one or more fibrous-element forming materials may comprise a polar solvent-soluble material, such as an alcohol-soluble material and/or a water-soluble material.

The one or more fibrous-element forming materials may comprise a non-polar solvent-soluble material.

The one or more fibrous-element forming materials may comprise a water-soluble material and be free (less than about 5% and/or less than about 3% and/or less than about 1% and/or 0% by weight on a dry fibrous element basis and/or dry water-soluble fibrous structure basis) of water-insoluble materials.

The one or more fibrous-element forming materials may be a film-forming material. The one or more fibrous-element forming materials may be synthetic or of natural origin and it may be chemically, enzymatically, and/or physically modified.

The one or more fibrous-element forming materials comprise one or more hydroxyl polymers comprising a natural starch and/or a modified starch.

The one or more hydroxyl polymers may have a weight average molecular weight of from about 10,000 g/mol to about 40,000,000 g/mol, preferably from 100,000 g/mol to about 40,000,000 g/mol, more preferably from 1,000,000 g/mol to about 40,000,000 g/mol, even more preferably from 3,000,000 g/mol to about 40,000,000 g/mol, most preferably from 3,000,000 g/mol to about 40,000,000 g/mol.

Alternatively, the one or more hydroxyl polymers may have a weight average molecular weight of from about 10,000 g/mol to about 40,000,000 g/mol, preferably from about 100,000 g/mol to about 10,000,000 g/mol, more preferably from about 1,000,000 g/mol to about 3,000,000 g/mol according to the weight average molecular weight test method.

The one or more hydroxyl polymers comprising a natural starch and/or a modified starch may be not cross-linked. When a natural starch and/or a modified starch is not cross-linked, the resulting fibrous structure can be relatively better readily water-soluble.

The one or more hydroxyl polymers may comprise a natural starch, a starch derivative and/or a starch copolymer. Alternatively, the one or more hydroxyl polymers may comprise ethoxylated starch. Alternatively, the one or more hydroxyl polymers may comprise acid-thinned starch. Alternatively, the one or more hydroxyl polymers may comprise Dent corn starch.

A natural starch may be modified chemically or enzymatically, as well known in the art. For example, the natural starch may be acid-thinned, hydroxy-ethylated, hydroxypropylated, ethersuccinylated or oxidized.

Naturally occurring starch may be generally a mixture of linear amylose and branched amylopectin polymer of D-glucose units. The amylose is a substantially linear polymer of D-glucose units joined by (1,4)-α-D links. The amylopectin is a highly branched polymer of D-glucose units joined by (1,4)-α-D links and (1,6)-α-D links at the branch points. Naturally occurring starch typically contains relatively high levels of amylopectin, for example, corn starch (64-80% amylopectin), waxy maize (93-100% amylopectin), rice (83-84% amylopectin), potato (about 78% amylopectin), and wheat (73-83% amylopectin). Though all starches are potentially useful herein, relatively high amylopectin natural starches derived from agricultural sources may be preferred, as relatively high amylopectin natural starches derived from agricultural sources may offer the advantages of being abundant in supply, easily replenishable and inexpensive.

The one or more hydroxyl polymers may comprise a natural starch having a level of amylopectin greater than about 75% by weight of starch, preferably greater than about 90% by weight of starch, more preferably greater than about 98% by weight of starch, even more preferably greater than about 99% by weight of starch.

Alternatively, the one or more hydroxyl polymers may comprise a natural starch having an amylopectin content from about 20% to about 100%, more typically from about 40% to about 90%, even more typically from about 60% to about 85% by weight of the starch.

The natural starch may be selected from the group consisting of corn starch, potato starch, sweet potato starch, wheat starch, sago palm starch, tapioca starch, rice starch, soybean starch, arrow root starch, amioca starch, bracken starch, lotus starch, waxy maize starch, high amylose corn starch, and mixtures thereof.

Chemical modifications of starch may typically include acid or alkaline-catalyzed hydrolysis and chain scission (oxidative and/or enzymatic) to reduce molecular weight and molecular weight distribution. Suitable compounds for chemical modification of starch include organic acids such as citric acid, acetic acid, glycolic acid, and adipic acid; inorganic acids such as hydrochloric acid, sulfuric acid, nitric acid, phosphoric acid, boric acid, and partial salts of polybasic acids, e.g., $KH_2PO_4$, $NaHSO_4$; group Ia or IIa metal hydroxides such as sodium hydroxide, and potassium hydroxide; ammonia; oxidizing agents such as hydrogen peroxide, benzoyl peroxide, ammonium persulfate, potassium permanganate, hypochloric salts, and the like; and mixtures thereof.

A modified starch may be defined as a starch that has been modified chemically or enzymatically. The modified starch may be contrasted with a native starch, which is a starch that has not been modified, chemically or otherwise, in any way.

Chemical modifications may also include derivatization of starch by reaction of its hydroxyl groups with alkylene oxides, and other ether-, ester-, urethane-, carbamate-, or isocyanate-forming substances. The degree of substitution of the chemically modified starch may from 0.001 to 3.0, and more specifically from 0.003 to 0.2. Biological modifications of starch may include bacterial digestion of the carbohydrate bonds, or enzymatic hydrolysis using enzymes such as amylase, amylopectase, and the like.

The modified starch may be thus selected from the group consisted of hydroxyethylated starch, hydroxypropylated starch, ethersuccinylated starch, acetylated starch, carbamate starch, and mixtures thereof.

In order to generate rheological properties suitable for high-speed fibrous element spinning processes, the molecular weight of the natural, unmodified starch may be reduced. The optimum molecular weight may be dependent on the type of starch used. For example, a starch with a low level of amylose component, such as a waxy maize starch, disperses rather easily in an aqueous solution with the application of heat and does not retrograde or recrystallize significantly.

Hence, the natural starch may comprise a waxy maize starch having a weight average molecular weight of from about 500,000 g/mol to about 40,000,000 g/mol according to the weight average molecular weight test method.

Modified starches such as hydroxyethylated Dent corn starch, which contains about 25% amylose, or oxidized Dent corn starch may tend to retrograde more than waxy maize starch but less than acid thinned starch. This retrogradation, or recrystallization, acts as a physical crosslinking to effectively raise the weight average molecular weight of the starch in aqueous solution.

Hence, the modified starch may comprise a hydroxyethylated starch having a weight average molecular weight of from about 200,000 g/mol to about 10,000,000 g/mol according to the weight average molecular weight test method.

Alternatively, an appropriate weight average molecular weight for a typical commercially available hydroxyethylated Dent corn starch with 2 wt. % hydroxyethylation or oxidized Dent corn starch may be from about 200,000 g/mol to about 10,000,000 g/mol.

Alternatively, for ethoxylated starches with higher degrees of ethoxylation, for example a hydroxyethylated Dent corn starch with 5 wt % hydroxyethylation, a weight average molecular weights of up to 40,000,000 g/mol may be suitable.

Alternatively, for acid thinned Dent corn starch, which tends to retrograde more than oxidized Dent corn starch, the appropriate weight average molecular weight may be from about 100,000 g/mol to about 15,000,000 g/mol.

The weight average molecular weight of starch may also be reduced to a desirable range by physical/mechanical degradation (e.g., via the thermomechanical energy input of the processing equipment).

The natural starch may be hydrolyzed in the presence of an acid catalyst to reduce the molecular weight and molecular weight distribution of the composition. The acid catalyst may be selected from the group consisting of hydrochloric acid, sulfuric acid, phosphoric acid, citric acid, ammonium chloride and any combination thereof. Also, a chain scission agent may be incorporated into a spinnable starch composition such that the chain scission reaction takes place substantially concurrently with the blending of the starch with other components. Non-limiting examples of oxidative chain scission agents suitable for use herein may include ammonium persulfate, hydrogen peroxide, hypochlorite salts, potassium permanganate, and mixtures thereof. Typically, the chain scission agent may be added in an amount effective to reduce the weight average molecular weight of the starch to the desirable range. It is found that compositions having modified starches in the suitable weight average molecular weight ranges can have suitable shear viscosities, and thus improve processability of the composition. The improved processability may be evident in less interruptions of the process (e.g., reduced breakage, shots, defects, hang-ups) and better surface appearance and strength properties of the final water-soluble personal cleansing product, such as the water-soluble fibrous structure.

The plurality of fibrous elements may be void of thermoplastic, water-insoluble polymers.

The one or more fibrous element-forming materials may be present in a fibrous-element-forming composition at an amount of from about 20% to about 50%, preferably from about 30% to about 50%, more preferably from about 35% to about 48% by weight of the fibrous-element-forming composition.

The one or more fibrous element-forming materials may be present in a fibrous element and/or fibrous structure, at a level of from about 50% to about 100%, preferably from about 60% to about 98%, more preferably from about 75% to about 95% by weight of the fibrous element and/or fibrous structure.

Other Polymers

The one or more fibrous element-forming materials may further comprise one or more hydroxyl polymers selecting from the group of polyols, such as polyvinyl alcohol, polyvinyl alcohol derivatives, polyvinyl alcohol copolymers, chitosan, chitosan derivatives, chitosan copolymers, cellulose, cellulose derivatives such as cellulose ether and ester derivatives, cellulose copolymers, hemicellulose, hemicellulose derivatives, hemicellulose copolymers, gums, arabinans, galactans, proteins, and mixtures thereof.

Alternatively, or also, the one or more fibrous element-forming materials may further comprise, other polymers, such as non-hydroxyl polymers.

The non-hydroxyl polymer may exhibit a weight average molecular weight from about 500,000 g/mol to about 10,000,000 g/mol, preferably from about 750,000 g/mol to about 5,000,000 g/mol, more preferably from about 1,000,000 g/mol to about 2,500.00 g/mol, even more preferably from about 1,250,000 g/mol to about 2,000,000 g/mol, most preferably from about 1,500,000 g/mol to about 1,750,000 g/mol.

The non-hydroxyl polymer may exhibit a polydispersity of greater than 1.10 and/or at least 1.20 and/or at least 1.30 and/or at least 1.32 and/or at least 1.40 and/or at least 1.45

The one or more fibrous element-forming materials may further comprise one or more non-hydroxyl polymers selecting from the group of polyacrylamide and derivatives such as carboxyl modified polyacrylamide polymers and copolymers including polyacrylic, poly(hydroxyethyl acrylic), polymethacrylic acid and their partial esters; vinyl polymers including polyvinyl alcohol, polyvinylpyrrolidone, and the like; polyamides; polyalkylene oxides such as polyethylene oxide and mixtures thereof. Copolymers or graft copolymers made from mixtures of monomers selected from the aforementioned polymers are also suitable herein. Non-limiting examples of commercially available polyacrylamides include nonionic polyacrylamides such as N300 from Kemira® or Hyperfloc® NF221, NF301, and NF241 from Hychem™, Inc.

The non-hydroxyl polymers may be present in an amount of from about 0.01% to about 10%, preferably from about 0.05% to about 5%, more preferably from about 0.075% to about 2.5%, even more preferably from about 0.1% to about 1%, by weight of the fibrous element-forming composition, filament and/or fibrous structure.

The non-hydroxyl polymer may comprise a linear polymer. The non-hydroxyl polymer may comprise a long chain branched polymer. The non-hydroxyl polymer may be compatible with the hydroxyl polymer at a concentration greater than the non-hydroxyl polymer's entanglement concentration $C_e$.

Non-limiting examples of suitable non-hydroxyl polymers may be selected from the group consisting of: polyacrylamide and its derivatives; polyacrylic acid, polymethacrylic acid and their esters; polyethyleneimine; copolymers made from mixtures of the aforementioned polymers; and mixtures thereof. The non-hydroxyl polymer may comprise polyacrylamide.

The plurality of fibrous elements may comprise two or more non-hydroxyl polymers, such as two or more polyacrylamides, such at two or more different weight average molecular weight polyacrylamides.

Preferred, the one or more fibrous element-forming materials may further comprise one or more polymers selected from the group consisting of polyacrylamide, carboxyl modified polyacrylamide, polyacrylic acid, poly(hydroxyethyl acrylic acid), polymethacrylic acid and partial esters, polyvinyl alcohol, carboxymethyl cellulose, hydroxypropylmethyl cellulose, polyvinylpyrrolidone, polyamide, polyethylene oxide, and mixtures thereof.

Most preferred, the one or more fibrous element-forming materials may comprise a natural starch and/or a modified starch, as defined hereinbefore, and may further comprise one or more polyvinyl alcohols.

The one or more fibrous-element forming materials may further comprise one or more polyvinyl alcohols. The one or more polyvinyl alcohols may exhibit a weight average molecular weight of from about 10,000 g/mol to about 40,000,000 g/mol, preferably from about 20,000 g/mol to about 30,000,000 g/mol, more preferably from about 35,000 g/mol to about 20,000,000 g/mol, even more preferably from about 40,000 g/mol to about 5,000,000 g/mol, most preferably from about 40,000 g/mol to about 500,000 g/mol.

The one or more fibrous-element forming materials may preferably further comprise two or more polyvinyl alcohols. In that case, one of the two or more polyvinyl alcohols may exhibit a weight average molecular weight of from about 10,000 g/mol to about 100,000 g/mol, preferably from about 20,000 g/mol to about 50,000 g/mol, more preferably from about 25,000 g/mol to about 45,000 g/mol, and the other of two or more polyvinyl alcohols may exhibit a weight average molecular weight of from about 105,000 g/mol to about 40,000,000 g/mol, preferably from about 110,000 g/mol to about 20,000,000 g/mol, more preferably from about 120,000 g/mol to about 500,000 g/mol.

Alternatively, the one or more fibrous element-forming materials may comprise a natural starch and/or a modified starch, as defined hereinbefore, and may further comprise one or more polyacrylamides.

Alternatively, the one or more fibrous element-forming materials may comprise a natural starch and/or a modified starch, as defined hereinbefore, and may further comprise one or more polyvinylpyrrolidones.

Coating with an Oily Composition

The water-soluble personal cleansing product may comprise one or more surfaces, preferably a top surface and a bottom surface, wherein the one or more surfaces, preferably the top surface, is coated with an oily composition, wherein the oily composition comprises one or more oil ingredients. Such water-soluble personal cleansing product coated with an oily composition can help for removing make-up products from the skin, in a gentle manner.

The one or more oil ingredients may be selected from the group consisting of butter, C12-C18 alkyl triglycerides, caprylic/capric/lauric triglyceride, caprylic/capric/linoleic triglyceride, caprylic/capric/stearic triglyceride, caprylic/capric triglyceride, cocoa butter, C10-C18 alkyl triglycerides, egg oil, soybean oil, epoxidized soybean oil, glyceryl triacetyl hydroxystearate, glyceryl triacetyl ricinoleate, glycosphingolipids, hydrogenated castor oil, hydrogenated castor oil laurate, hydrogenated coconut oil, hydrogenated C12-C18 alkyl triglycerides, hydrogenated fish oil, hydrogenated lard, hydrogenated menhaden oil, hydrogenated mink oil, hydrogenated orange roughy oil, hydrogenated shark liver oil, hydrogenated tallow, hydrogenated vegetable oil, lanolin and lanolin derivatives, lanolin alcohol, lard, lauric/palmitic/oleic triglyceride, lesquerella oil, maleated soybean oil, neatsfoot oil, oleic/linoleic triglyceride, oleic/palmitic/lauric/myristic/linoleic triglyceride, oleostearine, olive husk oil, omental lipids, pengawar djambi oil, pentadesma butter, phospholipids, shea butter, tallow, tribehenin, tricaprin, tricaprylin, triheptanoin, trihydroxymethoxystearin, trihydroxystearin, triisononanoin, triisostearin, trilaurin, trilinolein, trilinolenin, trimyristin, trioctanoin, triolein, tripalmitin, trisebacin, tristearin, triundecanoin, and mixtures thereof.

The one or more oil ingredients may comprise an ester selected from the group consisting of isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, and oleyl adipate, and mixtures thereof.

The oily composition may comprise a blend of two or more oil ingredients selected from the group consisting of butter, C12-C18 alkyl triglycerides, caprylic/capric/lauric triglyceride, caprylic/capric/linoleic triglyceride, caprylic/capric/stearic triglyceride, caprylic/capric triglyceride, cocoa butter, C10-C18 alkyl triglycerides, egg oil, soybean oil, epoxidized soybean oil, glyceryl triacetyl hydroxystearate, glyceryl triacetyl ricinoleate, glycosphingolipids, hydrogenated castor oil, hydrogenated castor oil laurate, hydrogenated coconut oil, hydrogenated C12-C18 alkyl triglycerides, hydrogenated fish oil, hydrogenated lard, hydrogenated menhaden oil, hydrogenated mink oil, hydrogenated orange roughy oil, hydrogenated shark liver oil, hydrogenated tallow, hydrogenated vegetable oil, lanolin and lanolin derivatives, lanolin alcohol, lard, lauric/palmitic/oleic triglyceride, lesquerella oil, maleated soybean oil, neatsfoot oil, oleic/linoleic triglyceride, oleic/palmitic/lauric/myristic/linoleic triglyceride, oleostearine, olive husk oil, omental lipids, pengawar djambi oil, pentadesma butter, phospholipids, shea butter, tallow, tribehenin, tricaprin, tricaprylin, triheptanoin, trihydroxymethoxystearin, trihydroxystearin, triisononanoin, triisostearin, trilaurin, trilinolein, trilinolenin, trimyristin, trioctanoin, triolein, tripalmitin, trisebacin, tristearin, triundecanoin, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, and oleyl adipate, and mixtures thereof.

The oily composition may comprise a blend of an oil ingredient and an ester, wherein the oil ingredient is selected from the group consisting of caprylic/capric/lauric triglyceride, caprylic/capric/linoleic triglyceride, caprylic/capric/stearic triglyceride, caprylic/capric triglyceride, lauric/palmitic/oleic triglyceride, oleic/linoleic triglyceride, oleic/palmitic/lauric/myristic/linoleic triglyceride, soybean oil, and mixtures thereof; wherein the ester is selected from the group consisting of isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, and oleyl adipate, and mixtures thereof; and wherein the blend of the oil ingredient and the ester may comprise a weight ratio of the total level of the oil ingredient to the ester from 80:20 to 40:60, preferably from 70:30 to 45:55, more preferably from 60:40 to 50:50, most preferably from 55:45 to 52:48.

Most preferably, the oily composition may comprise a blend of caprylic/capric triglyceride and isopropyl palmitate with a weight ratio of the total level of caprylic/capric triglyceride to isopropyl palmitate is from 60:40 to 50:50, preferably from 55:45 to 52:48. Such preferred water-soluble personal cleansing product coated with the oily composition having the blend of caprylic/capric triglyceride and isopropyl palmitate can help for removing water-resistant make-up products, e.g. long-lasting products such as transfer-resistant foundations, long-lasting lipsticks, waterproof mascaras or double-action mascaras.

Hence, the oily composition as described above coated on the water-soluble personal cleansing product can help for removing fatty residues, e.g. sebum excess, and make-up residues from the skin, especially water resistant make-up residues such as waterproof mascaras.

Coating with a Cleansing Composition

Alternatively, the water-soluble personal cleansing product may comprise one or more surfaces, preferably a top surface and a bottom surface, wherein the one or more surfaces, preferably the top surface, is coated with a cleansing composition comprising one or more surfactants.

The plurality of fibrous elements is substantially free of surfactant; however, the water-soluble personal cleansing product may be coated with a cleansing composition comprising one or more surfactants.

In that case, the cleansing composition is substantially free of alkyl sulfate and alkyl ether sulfate type of surfactants.

Such water-soluble personal cleansing product coated with the cleansing composition comprising the one or more surfactants, the cleansing composition being substantially free of alkyl sulfate and alkyl ether sulfate type of surfactants can alternatively help for removing make-up products from the skin, in a gentle manner.

The one or more surfactants may comprise at least one glutamate surfactant according to the general formula (I):

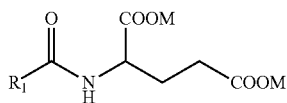

(I)

wherein $R_1$ is a saturated or unsaturated, straight or branched alkyl or alkenyl chain with from 5 to 20 carbon atoms, preferably with from 7 to 17 carbon atoms, more preferably with from 9 to 13 carbon atoms; and M is H, ammonium, triethanolammonium (TEA), sodium or potassium and mixtures thereof.

The at least one glutamate surfactant may selected from the group consisting of sodium cocoyl glutamate, disodium cocoyl glutamate, potassium cocoyl glutamate, dipotassium cocoyl glutamate, ammonium cocoyl glutamate, diammonium cocoyl glutamate, sodium lauroyl glutamate, disodium lauroyl glutamate, potassium lauroyl glutamate, dipotassium lauroyl glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallowoyl glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallowoyl glutamate, sodium cocoyl/palmoyl/sunfloweroyl glutamate, sodium hydrogenated tallowoyl glutamate, sodium olivoyl glutamate, disodium olivoyl glutamate, sodium palmoyl glutamate, disodium palmoyl glutamate, TEA-cocoyl glutamate, TEA-hydrogenated tallowoyl glutamate, TEA-lauroyl glutamate, and mixtures thereof.

Preferably, the at least one glutamate surfactant may be selected from the group consisting of sodium cocoyl glutamate, disodium cocoyl glutamate, potassium cocoyl glutamate, dipotassium cocoyl glutamate, ammonium cocoyl glutamate, diammonium cocoyl glutamate, sodium lauroyl glutamate, disodium lauroyl glutamate, potassium lauroyl glutamate, dipotassium lauroyl glutamate, sodium capryloyl glutamate, disodium capryloyl glutamate, potassium capryloyl glutamate, dipotassium capryloyl glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, TEA-cocoyl glutamate, and mixtures thereof More preferably, the at least one glutamate surfactant may be selected from the group consisting of sodium cocoyl glutamate, disodium cocoyl glutamate, potassium cocoyl glutamate, dipotassium cocoyl glutamate, ammonium cocoyl glutamate, diammonium cocoyl glutamate, TEA-cocoyl glutamate, and mixtures thereof.

The total level of the at least one glutamate surfactant may be from about 20% to about 95% by weight of the cleansing composition. Preferably, the total level of the at least one glutamate surfactant may be from about 25% to about 90% by weight of the cleansing composition. More preferably, the total level of the at least one glutamate surfactant may be from about 30% to about 70% by weight of the cleansing composition.

The one or more surfactants may also comprise a co-surfactant by weight of the composition, wherein the co-surfactant is selected from the group consisting of an anionic surfactant being not a glutamate surfactant, a non-ionic surfactant, an amphoteric surfactant, a zwitterionic surfactant, and mixtures thereof.

The total level of the co-surfactant may be from about 2% to about 30% by weight of the cleansing composition. Preferably, the total level of the co-surfactant may be from about 5% to about 25% by weight of the cleansing composition. More preferably, the total level of the co-surfactant may be from about 7% to about 20% by weight of the cleansing composition.

The anionic surfactant being not a glutamate surfactant may be selected from the group consisting of an isethionate surfactant, a sarcosinate surfactant, a glycinate surfactant, an alanitate surfactant, a sulfosuccinate surfactant, a sulfonate surfactant, a sulfoacetate surfactant, a glucose carboxylate surfactant, an alkyl ether carboxylate surfactant, a taurate surfactant, and mixtures thereof. Each anionic surfactant just listed above will be described in more details below.

The one or more surfactants may alternatively or also comprise at least one isethionate surfactant according to the general formula (II):

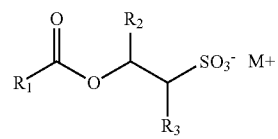

(II)

wherein $R_1$ is a saturated or unsaturated, straight or branched, alkyl or alkenyl chain with from 6 to 30 carbon atoms, preferably from 8 to 22 carbon atoms, more preferably from 9 to 18 carbon atoms, $R_2$ and $R_3$ are each independently H or ($C_1$-$C_4$) alkyl, preferably wherein ($C_1$-$C_4$) alkyl is methyl, and $M^+$ is an alkali metal, preferably lithium, sodium, potassium; or $M^+$ is an alkali-earth metal, preferably magnesium; or $M^+$ is an ammonium or a substituted ammonium cation.

The isethionate surfactant may be selected from the group consisting of sodium lauroyl isethionate, sodium lauroyl methyl isethionate, sodium oleoyl isethionate, sodium oleoyl methyl isethionate, sodium stearoyl isethionate, sodium stearoyl methyl isethionate, sodium myristoyl isethionate, sodium myristoyl methyl isethionate, sodium palmitoyl isethionate, sodium palmitoyl methyl isethionate, sodium cocoyl isethionate, sodium cocoyl methyl isethionate, a blend of stearic acid and sodium cocoyl isethionate, ammonium cocoyl isethionate, ammonium cocoyl methyl isethionate, and mixtures thereof.

The isethionate surfactant may be preferably selected from the group consisting of sodium lauroyl isethionate, sodium lauroyl methyl isethionate, sodium oleoyl isethionate, sodium stearoyl isethionate, sodium myristoyl isethionate, sodium palmitoyl isethionate, sodium cocoyl isethionate, ammonium cocoyl isethionate, and mixtures thereof.

The isethionate surfactant may be more preferably selected from the group consisting of sodium lauroyl isethionate, sodium lauroyl methyl isethionate, sodium stearoyl isethionate, sodium myristoyl isethionate, sodium cocoyl isethionate, ammonium cocoyl isethionate, and mixtures thereof.

The isethionate surfactant may be even more preferably selected from the group consisting of sodium lauroyl isethionate, sodium cocoyl isethionate, ammonium cocoyl isethionate, and mixtures thereof.

Corresponding commercial products are available, for example, from the company Innospec under the trade name "Iselux®" and from Clariant® or Uniqema™ under the trade names "Hostapon®" or "Arlatone®". Examples of other commercial fatty acyl isethionates that may be used can be Hostapon® surfactants from Clariant® such as for sodium cocoyl isethionate: Hostapon® SCI-85C, Hostapon® SCI-78C, or a blend of stearic acid with sodium cocoyl isethionate: Hostapon® SCI-65C. Examples of other commercial fatty acyl isethionates that may be used can be "Jordapon®" surfactants from BASF® such as Jordapon® CI prill or Jordapon® CI65; and sodium cocoyl isethionate from Yongan® Daily Chemical Co. such as YA-SCI-85® or YA-SCI-65®.

The sarcosinate surfactant may have the general formula (III):

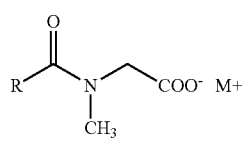

(III)

wherein R is a saturated or unsaturated, straight or branched alkyl or alkenyl, preferably alkyl chain with 7 to 17 carbon atoms, preferably with 9 to 13 carbon atoms and M$^+$ is H, a sodium, potassium, ammonium or triethanolammonium cation.

The sarcosinate surfactant may be selected from the group consisting of sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lauroyl glutamate/lauroyl sarcosinate, disodium lauroamphodiacetate, lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and mixtures thereof.

Preferably, the sarcosinate surfactant may be selected from the group consisting of sodium lauroyl sarcosinate, sodium myristoyl sarcosinate, sodium cocoyl sarcosinate, and mixtures thereof.

The glycinate surfactant may be selected from the group consisting of sodium cocoyl glycinate, sodium lauroyl glycinate, and mixture thereof.

The alaninate surfactant may be selected from the group consisting of sodium cocoyl alaninate, sodium lauroyl alaninate, sodium N-dodecanoyl-1-alaninate, and mixture thereof.

The sulfosuccinate surfactant may be selected from the group consisting of disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and mixtures thereof.

The sulfonate surfactant may be selected from the group consisting of alpha olefin sulfonates, linear alkylbenzene sulfonates, sodium laurylglucosides hydroxypropylsulfonate, and mixtures thereof.

The sulfoacetate surfactant may be selected from the group consisting of sodium lauryl sulfoacetate, ammonium lauryl sulfoacetate, and mixture thereof.

The glucose carboxylate surfactant may be selected from the group consisting of sodium lauryl glucoside carboxylate, sodium cocoyl glucoside carboxylate, and mixtures thereof.

The alkyl ether carboxylate surfactant may be selected from the group consisting of sodium laureth-4 carboxylate, laureth-5 carboxylate, laureth-13 carboxylate, sodium C12-13 pareth-8 carboxylate, sodium C12-15 pareth-8 carboxylate and mixtures thereof.

The taurate surfactant may be selected from the group consisting of sodium methyl cocoyl taurate, sodium methyl lauroyl taurate, sodium methyl oleoyl taurate, and mixtures thereof.

The anionic surfactant being not a glutamate surfactant may comprise a lactate or lactylate. Non-limiting example of lactates can include sodium lactate. Non-limiting examples of lactylates can include sodium lauroyl lactylate, sodium cocoyl lactylate, and mixture thereof.

The total level of the anionic surfactant being not a glutamate surfactant may be from about 0.5% to about 20% by weight of the cleansing composition. Preferably, the total level of the anionic surfactant being not a glutamate surfactant may be from about 0.5% to about 15% by weight of the cleansing composition. More preferably, the total level of the anionic surfactant being not a glutamate surfactant may be from about 1% to about 10% by weight of the cleansing composition.

The one or more surfactants may comprise a non-ionic surfactant. The non-ionic surfactant may be selected from the group consisting alkyl polyglucoside, alkyl glycoside, acyl glucamide and mixtures thereof.

In that case, alkyl is defined as a saturated or unsaturated, straight or branched alkyl chain with 6 to 30 carbon atoms, preferably with 8 to 22 carbon atoms, more preferably with 9 to 18 carbon atoms. In that case, acyl is defined as of formula R—C(O)—, wherein R is a saturated or unsaturated, straight or branched alkyl or alkenyl, preferably alkyl chain with 6 to 30 carbon atoms, preferably with 8 to 22 carbon atoms, more preferably with 9 to 18 carbon atoms.

The alkyl glucoside may be selected from the group consisting of decyl glucoside, cocoyl glucoside, lauroyl glucoside, and mixtures thereof.

The acyl glucamide may be selected from the group consisting of lauroyl/myristoyl methyl glucamide, caproyl/capryloyl methyl glucamide, cocoyl methyl glucamide and mixtures thereof.

Preferably, the non-ionic surfactant may be selected from the group consisting of cocoamide monoethanolamine, lauramide monoethanolamine, cocoyl glucoside, lauroyl glucoside, decyl glucoside, and mixtures thereof.

The total level of the non-ionic surfactant may be from about 0.1% to about 10% by weight of the cleansing composition. Preferably, the total level of the non-ionic surfactant may be from about 0.1% to about 5% by weight of the cleansing composition. More preferably, the total level of the non-ionic surfactant may be from about 0.5% to about 3% by weight of the cleansing composition.

Suitable amphoteric or zwitterionic surfactants can include those described in U.S. Pat. Nos. 5,104,646 and 5,106,609.

Amphoteric surfactants can include those that can be broadly described as derivatives of aliphatic secondary and tertiary amines in which an aliphatic radical can be straight or branched chain and wherein an aliphatic substituent can contain from 8 to 18 carbon atoms such that one carbon atom can contain an anionic water solubilizing group, e.g., carboxy, sulfonate, phosphate, or phosphonate. Examples of compounds falling within this definition can be sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378.

The amphoteric surfactant described herein may preferably selected from the group consisting of sodium lauroamphoacetate, sodium cocoamphoacetate, disodium lauroamphodiacetate, disodium cocodiamphoacetate, and mixtures thereof.

Zwitterionic surfactants suitable for use in the co-surfactants described herein may include those that are broadly described as derivatives of aliphatic quaternary ammonium, phosphonium, and sulfonium compounds, in which the aliphatic radicals can be straight or branched chains, and wherein one of the aliphatic substituents can contain from 8 to 18 carbon atoms and one can contain an anionic group, e.g., carboxy, sulfonate, phosphate, or phosphonate.

Hence, the one or more surfactants may comprise at least an amphoteric or zwitterionic surfactant selected from the group consisting of cocamidopropyl betaine, lauramidopropyl betaine, coco-betaine, lauryl betaine, lauryl hydroxysultaine, cocamidopropyl hydroxysultaine, coco-hydroxysultaine, coco-sultaine, lauryl sultaine, sodium cocoamphoacetate, disodium cocoamphodiacetate, sodium lauroamphoacetate, disodium lauroamphodiacetate, lauramine oxide, and mixtures thereof.

Examples of betaine zwitterionic surfactants may include coco dimethyl carboxymethyl betaine, cocoamidopropyl betaine (CAPB), coco-betaine, lauryl amidopropyl betaine (LAPB), oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. Examples of sulfobetaines may include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof.

Other Ingredients

The water-soluble personal cleansing product, and/or the water-soluble fibrous structure is free of preservatives. The water-soluble personal cleansing product, and/or the water-soluble fibrous structure is free of perfumes. Providing a water-soluble personal cleansing product, and/or a water-soluble fibrous structure free of preservatives and/or free of perfumes can allow preventing skin irritation typically generated due to the presence of preservative systems or perfumes.

The plurality of fibrous elements may comprise a plasticizer selected from the group consisting of glycerin, diglycerin, propylene glycol, ethylene glycol, butylene glycol, pentylene glycol, cyclohexane dimethanol, hexanediol, 2,2, 4-trimethylpentane-1,3-diol, polyethylene glycol with a weight average molecular weight from about 200 g/mol to about 600 g/mol, pentaerythritol, sorbitol, manitol, lactitol, fructose, glucose, sucrose, maltose, lactose, high fructose corn syrup solids, dextrins, ascorbic acid, and mixtures thereof.

Preferably, the plasticizer may be selected from the group consisting of glycerin, ethylene glycol, polyethylene glycol, propylene glycol, glycidol, urea, sorbitol, xylitol, maltitol, sugars, ethylene bisformamide, amino acids, and mixtures thereof.

The total level of the plasticizer may be from about 1% to about 40% by weight on a dry fibrous element basis and/or a dry water-soluble fibrous structure basis; preferably from about 2% to about 30% by weight on a dry fibrous element basis and/or a dry water-soluble fibrous structure basis; more preferably from about 5% to about 20% by weight on a dry fibrous element basis and/or a dry water-soluble fibrous structure basis.

The plurality of fibrous elements being substantially free of surfactant may comprise as a process aid a sulfosuccinate surfactant. A non-limiting example of a suitable sulfosuccinate surfactant comprises Aerosol® AOT (a sodium dioctyl sulfosuccinate) and/or Aerosol® MA-80 (a sodium dihexyl sulfosuccinate), which are commercially available from Cytec®. The sulfosuccinate surfactant may only be present at a level of from about 0% to about 1%, preferably from about 0.05% to about 0.95%, more preferably from about 0.1% to about 0.9% by weight of on a dry fibrous element basis and/or a dry water-soluble fibrous structure basis.

Method of Manufacture, Product Forms and Uses

Method of Manufacture

The water-soluble personal cleansing product comprising a water-soluble fibrous structure, includes a plurality of fibrous elements. The plurality of fibrous elements may be made by any suitable process.

The plurality of fibrous elements of the water-soluble fibrous structure may be obtainable by a process providing a fibrous element-forming composition, wherein the fibrous element-forming composition is an aqueous composition comprising one or more fibrous element-forming materials; and spinning the fibrous element-forming composition into a plurality of fibrous elements forming a water-soluble fibrous structure comprising a plurality of fibrous elements, preferably a plurality of filament elements.

A method of making a water-soluble personal cleansing product comprising a water-soluble fibrous structure as defined hereinbefore is provided and comprises the following steps, preferably in that order:

(a) providing a fibrous element-forming composition, wherein the fibrous element-forming composition is an aqueous composition comprising one or more fibrous element-forming materials; and (b) spinning the fibrous element-forming composition into a plurality of fibrous elements forming a water-soluble fibrous structure comprising a plurality of fibrous elements, preferably a plurality of filament elements.

Spinning the fibrous element-forming composition may be carried out via a spinning die, into the plurality of fibrous elements, such as filaments and/or fibers, comprising the one or more fibrous element-forming materials.

Spinning the fibrous element-forming composition into a plurality of fibrous elements may be provided by meltblowing, spunbonding, electro-spinning, and/or rotary spinning.

During the spinning step, any volatile solvent, such as water, present in the fibrous element-forming composition may be removed, by drying, as the plurality of fibrous elements is formed. Greater than about 30% and/or greater than about 40% and/or greater than about 50% of the weight of the fibrous element-forming composition's volatile solvent, such as water, may be removed during the spinning step, such as by drying the plurality of fibrous element being produced.

The fibrous element-forming composition may be spun into a plurality of fibrous elements by meltblowing. For example, the fibrous element-forming composition may be pumped from a tank to a meltblown spinnerette. Upon exiting one or more of the fibrous element-forming holes in the spinnerette, the fibrous element-forming composition is attenuated with air to create a plurality of fibrous elements. The plurality of fibrous elements may then be dried to remove any remaining solvent used for spinning, such as water.

The method of making a water-soluble personal cleansing product may further comprise the following steps, preferably in that order:
(c) at least partially drying the plurality of fibrous elements;
(d) depositing the partially dry plurality of fibrous elements on a surface to form a web of partially dry water-soluble fibrous structure;
(e) drying the partially dry water-soluble fibrous structure to a desired final moisture content;
(f) optionally applying a surface resident coating; and
(g) cutting the water-soluble fibrous structure into one or more shapes to form the water-soluble personal cleansing product.

The plurality of fibrous elements may be collected on a belt, such as a patterned belt to form a water-soluble fibrous structure comprising the plurality of fibrous elements.

Preferably, the total level of the one or more fibrous element-forming materials be from about 10% to about 99.9%, preferably from about 15% to about 99.8%, more preferably from about 15% to about 99.5% by weight of the fibrous element-forming composition.

The fibrous element-forming composition may comprise a plasticizer selected from the group consisting of glycerin, diglycerin, propylene glycol, ethylene glycol, butylene glycol, pentylene glycol, cyclohexane dimethanol, hexanediol, 2,2,4-trimethylpentane-1,3-diol, polyethylene glycol with a weight average molecular weight from about 200 g/mol to about 600 g/mol, pentaerythritol, sorbitol, manitol, lactitol, fructose, glucose, sucrose, maltose, lactose, high fructose corn syrup solids, dextrins, ascorbic acid, and mixtures thereof. Preferably, the plasticizer may be selected from the group consisting of glycerin, ethylene glycol, polyethylene glycol, propylene glycol, glycidol, urea, sorbitol, xylitol, maltitol, sugars, ethylene bisformamide, amino acids, and mixtures thereof.

The total level of the plasticizer may be from 1% to 40% by weight of the fibrous element-forming composition; preferably from 2% to 30% by weight of the fibrous element-forming composition; more preferably from 5% to 20% by weight of the fibrous element-forming composition.

The water-soluble personal cleansing product may further one or more scrubby particles within the plurality of fibrous elements. Scrubby particles can help for providing greater exfoliation to occur on the skin, which allows the consumer to experience a deep clean and to remove any dead skin cells during cleansing, except around the ocular area.

The one or more scrubby particles may comprise silica particles, preferably agglomerated silica. Agglomerated silica can break down into smaller granules as the consumer applies shear to the product, which provides a gentle exfoliation onto the skin.

Alternatively, the one or more scrubby particles may be selected from the group consisting of silica, agglomerated silica, polyethylene, polypropylene, jojoba esters, strawberry seeds, ground peach pits, walnut shell powder, corn kernel meal, polyhydroxy butyl co-valerate, stearyl stearate, jojoba wax ester, candelilla wax, sugar cellulose, polylactic acid (PLA), polyurethane (PU), polystyrene (PS), polymethylmethacrylate (PMMA), cross-linked polyesters, and mixtures thereof.

The one or more scrubby particles may have a size ranging from 80 μm to 500 μm, preferably from 100 μm to 400 μm, more preferably from 166 to 360 μm per Particle Size Distribution Test Method as disclosed herein.

The one or more scrubby particles may be added to the plurality of fibrous elements according to three ways:
1. Suspend the one or more scrubby particles in an oil material and spray the suspension onto the fibrous structure directly; or
2. Co-form the one or more scrubby particles with the plurality of fibrous elements during the spinning step. The one or more scrubby particles and the plurality of fibrous elements can intermingle with each other; or
3. Sandwich the one or more scrubby particles between two layers of fibrous structure layers followed by bonding the two layers together.

Forms and Uses

The water-soluble personal cleansing product may be in the form of a wipe, a pad, a facial cleansing wipe or facial cleansing pad for an adult or a baby, a bath tissue wipe, or a skin care substrate. The water-soluble personal cleansing product may be of any shapes.

The water-soluble personal cleansing products as described hereinbefore may be used for preventing ocular irritation when removing make-up material at an ocular region of a facial skin.

Also, the water-soluble personal cleansing products as described hereinbefore can be used for make-up removal from the skin, preferably for eye make-up removal. Especially, the water-soluble personal cleansing products can be used for make-up removal from the skin when the water-soluble personal cleansing product is coated with an oily composition as described above or alternatively with a cleansing composition comprising one or more surfactants as described above.

Kit

A kit for make-up removal from the skin, preferably for eye make-up removal, is provided and comprises:
i) a first water-soluble personal cleansing product comprising the water-soluble personal cleansing product as described hereinbefore, i.e. the one coated with the oily composition or alternatively the one coated with the cleansing composition; and
ii) a second water-soluble personal cleansing product, preferably a second water-soluble facial cleansing product comprising a water-soluble fibrous structure of the second water-soluble personal cleansing product;
wherein the water-soluble fibrous structure comprises a plurality of fibrous elements;
wherein the plurality of fibrous elements comprises:
one or more fibrous element-forming materials comprising one or more polyvinyl alcohol; and
one or more active agents present within the plurality of fibrous elements, wherein the one or more active agents comprise one or more surfactants, wherein the one or more surfactants comprise at least one glutamate surfactant as defined hereinbefore according to the general formula (I):

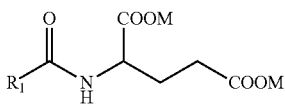

(I)

wherein R₁ is a saturated or unsaturated, straight or branched alkyl or alkenyl chain with from 5 to 20 carbon atoms, preferably with from 7 to 17 carbon atoms, more preferably with from 9 to 13 carbon atoms; and M is H, ammonium, triethanolammonium (TEA), sodium or potassium and mixtures thereof; and wherein the water-soluble fibrous structure of the second water-soluble personal cleansing product is substantially free of alkyl sulfate and alkyl ether sulfate type of surfactants.

Such kit can provide a dual benefit, namely the removal of any make-up residues from the skin and cleaning of the skin if any oily residues from the make-up residues remains, while being mild to the skin, and thus preventing any ocular irritation.

The one or more surfactants of the one or more active agents may be defined as the one or more surfactants of the cleansing composition as described above.

The one or more surfactants of the one or more active agents may comprise a co-surfactant by weight of the composition as define hereinbefore.

The one or more surfactants of the one or more active agents may comprise at least one isethionate surfactant according to the general formula (II) as defined hereinbefore.

The one or more surfactants of the one or more active agents may comprise a non-ionic surfactant as defined hereinbefore.

For the second water-soluble fibrous structure, the total level of the one or more fibrous element-forming materials may be from about 5% to about 80%, preferably from about 10% to about 75%, more preferably from about 20% to about 70% by weight on a dry fibrous element basis and/or a dry water-soluble fibrous structure basis, and the total level of the one or more active agents is from about 20% to about 95%, preferably from about 25% to about 90%, more preferably from about 30% to about 80% by weight on a dry fibrous element basis and/or a dry water-soluble fibrous structure basis.

For the second water-soluble fibrous structure, the one or more fibrous element-forming materials and the one or more active agents may present in the plurality of fibrous elements at a weight ratio of the total level of the one or more fibrous element-forming materials to the one or more active agents from about 0.1 to about 4.0, preferably from about 0.15 to about 2.0, more preferably from about 0.2 to about 1.5, even more preferably from about 0.5 to about 1.2; most preferably from about 0.5 to about 0.65 or from about 0.8 to about 1.2.

The one or more fibrous element-forming materials of the second water-soluble fibrous structure may comprise two or more different polyvinyl alcohols. In that case, one of the two or more polyvinyl alcohols may exhibit a weight average molecular weight of from about 10,000 g/mol to about 100,000 g/mol, preferably from about 20,000 g/mol to about 50,000 g/mol, more preferably from about 25,000 g/mol to about 45,000 g/mol, and the other of two or more polyvinyl alcohols may exhibit a weight average molecular weight of from about 105,000 g/mol to about 40,000,000 g/mol, preferably from about 110,000 g/mol to about 20,000,000 g/mol, more preferably from about 120,000 g/mol to about 500,000 g/mol.

A method of making the second water-soluble personal cleansing product as described hereinbefore comprising the second water-soluble fibrous structure as defined hereinbefore is provided and comprises the following steps, preferably in that order:
  (a) providing a fibrous element-forming composition, wherein the fibrous element-forming composition is an aqueous composition comprising one or more fibrous element-forming materials and one or more active agents; and
  (b) spinning the fibrous element-forming composition into a plurality of fibrous elements forming a water-soluble fibrous structure comprising a plurality of fibrous elements, preferably a plurality of filament elements.

Methods of Use

A method for make-up removal from the skin, preferably for eye make-up removal, optionally while preventing ocular irritation, is provided and comprises the following steps, preferably in that order:
a) providing the water-soluble personal cleansing product comprising the water-soluble fibrous structure and the oily composition coated on one or more surfaces of the water-soluble personal cleansing product, preferably on a top surface of the water-soluble personal cleansing product as described hereinbefore;
b) removing any make-up residues from the skin by applying the one or more surfaces, preferably the top surface of the water-soluble personal cleansing product comprising the oily composition; optionally rinsing with water.

Alternatively, a method for make-up removal from the skin, preferably for eye make-up removal, optionally while preventing ocular irritation, is provided and comprises the following steps, preferably in that order:
a) providing the water-soluble personal cleansing product comprising the water-soluble fibrous structure and the cleansing composition comprising one or more surfactants, wherein the cleansing composition is coated on one or more surfaces of the water-soluble personal cleansing product, preferably on a top surface of the water-soluble personal cleansing product as described hereinbefore;
b) removing any make-up residues from the skin by applying the one or more surfaces, preferably the top surface of the water-soluble personal cleansing product comprising the oily composition; optionally rinsing with water.

Each of the above methods for make-up removal from the skin may additionally comprise the following steps, preferably in that order:
c) providing a second water-soluble personal cleansing product, preferably a second water-soluble facial cleansing product, comprising a water-soluble fibrous structure of the second water-soluble personal cleansing product;
wherein the water-soluble fibrous structure comprises a plurality of fibrous elements;
wherein the plurality of fibrous elements comprises:
  one or more fibrous element-forming materials comprising one or more polyvinyl alcohol; and
  one or more active agents present within the plurality of fibrous elements, wherein the one or more active agents comprise one or more surfactants, wherein the one or more surfactants comprise at least one glutamate surfactant according to the general formula (I):

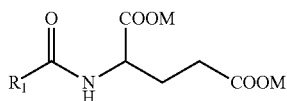

(I)

wherein $R_1$ is a saturated or unsaturated, straight or branched alkyl or alkenyl chain with from 5 to 20 carbon atoms, preferably with from 7 to 17 carbon atoms, more preferably with from 9 to 13 carbon atoms; and M is H, ammonium, triethanolammonium (TEA), sodium or potassium and mixtures thereof d) wetting the second water-soluble personal cleansing product with water to obtain a cleansing solution;

e) shearing the cleansing solution to generate lathering, preferably by rotating a palm of a user's hand against the cleansing solution; lathering and applying the cleansing solution to the skin; and f) rinsing with water.

Such method can provide a dual benefit, namely the removal of any make-up residues from the skin and cleansing of the skin if any oily residues from the make-up residues remains, while being mild to the skin, and thus preventing any ocular irritation.

Test Methods

It is understood that the test methods that are disclosed in the Test Methods Section of the present application should be used to determine the respective values of the parameters of Applicants' invention as such invention is described and claimed herein.

Unless otherwise specified, all tests described herein including those described under the Definitions section and the following test methods are conducted on samples that have been conditioned in a conditioned room at a temperature of 23° C.±1.0° C. and a relative humidity of 50%±2% for a minimum of 2 hours prior to the test. All tests are conducted under the same environmental conditions and in such conditioned room. All instruments are calibrated according to manufacturer's specifications.

Basis Weight Test Method

Basis weight is defined as the weight in $g/m^2$ of a sample being tested. It is determined by accurately weighing a known area of a sample using an appropriate balance, recording the weight and area of sample tested, applying the appropriate conversion factors, and finally calculating the basis weight in $g/m^2$ of the sample.

Basis weight is measured by cutting a sample from a single web, a stack of webs, or other appropriate plied up and weighing the sample using a top loading analytical balance with a resolution of ±0.001 g. The sample must be equilibrated at a temperature of 73±2° F. (23°±1° C.) and a relative humidity of 50% (±2%) for a minimum of two hours prior to cutting samples. During weighing, the balance is protected from air drafts and other disturbances using a draft shield. A precision cutting die, measuring 1.625×1.625 in (41.275×41.275 mm) is used to prepare all samples. Select usable sample areas which are clean, free of holes, tears, wrinkles and other defects.

For each sample use the die cutter described above to cut a sample, weigh the mass of the sample, and record the mass result to the nearest 0.001 g.

The Basis Weight is calculated in $g/m^2$ as follows:

Basis Weight=(Mass of sample)/(Area of sample).

Or specifically,

Basis Weight $(g/m^2)$=(Mass of sample (g))/(0.001704 $m^2$).

Report result to the nearest 0.1 $g/m^2$. Sample dimensions can be changed or varied using a similar precision cutter as mentioned above. If the sample dimension is decreased, then several samples should be measured, and the mean value reported as its basis weight.

Water Content Test Method

The water (or moisture) content present in one or more fibrous elements and/or water-soluble fibrous structure is measured using the following Water Content Test Method. A fibrous element and/or water-soluble fibrous structure or portion thereof ("sample") in the form of a pre-cut sheet is placed in a conditioned room at a temperature of 23° C.±1.0° C. and a relative humidity of 50%±2% for at least 24 hours prior to testing. Each fibrous structure sample has an area of at least 4 square inches (25.8 $cm^2$), but small enough in size to fit appropriately on the balance weighing plate. Under the temperature and humidity conditions mentioned above, using a balance with at least four decimal places, the weight of the sample is recorded every five minutes until a change of less than 0.5% of previous weight is detected during a 10-minute period. The final weight is recorded as the "equilibrium weight". Within 10 minutes, the samples are placed into the forced air oven on top of foil for 24 hours at 70° C.±2° C. at a relative humidity of 4%±2% for drying. After the 24 hours of drying, the sample is removed and weighed within 15 seconds. This weight is designated as the "dry weight" of the sample.

The water (moisture) content of the sample is calculated as follows:

$$\% \text{ Water in sample} = 100\% \times \frac{\left(\begin{array}{c}\text{Equilibrium weight of sample} - \\ \text{Dry weight of sample}\end{array}\right)}{\text{Dry weight of sample}}$$

The % Water (moisture) in sample for 3 replicates is averaged to give the reported % Water (moisture) in sample. Report results to the nearest 0.1%.

Diameter Test Method

The diameter of a discrete fibrous element or a fibrous element within a water-soluble fibrous structure is determined by using a Scanning Electron Microscope (SEM) or an Optical Microscope and an image analysis software. A magnification of 200 to 10,000 times is chosen such that the fibrous elements are suitably enlarged for measurement. When using the SEM, the samples are sputtered with gold or a palladium compound to avoid electric charging and vibrations of the fibrous element in the electron beam. A manual procedure for determining the fibrous element diameters is used from the image (on monitor screen) taken with the SEM or the optical microscope. Using a mouse and a cursor tool, the edge of a randomly selected fibrous element is sought and then measured across its width (i.e., perpendicular to fibrous element direction at that point) to the other edge of the fibrous element. A scaled and calibrated image analysis tool provides the scaling to get actual reading in μm. For fibrous elements within a water-soluble fibrous structure, several fibrous elements are randomly selected across the sample of the water-soluble fibrous structure using the SEM or the optical microscope. At least two portions of the water-soluble fibrous structure are cut and tested in this manner. Altogether at least 100 such measurements are made and then all data are recorded for statistical analysis. The recorded data are used to calculate average (mean) of the fibrous element diameters, standard deviation of the fibrous element diameters, and median of the fibrous element diameters.

Another useful statistic is the calculation of the amount of the population of fibrous elements that is below a certain upper limit. To determine this statistic, the software is programmed to count how many results of the fibrous element diameters are below an upper limit and that count (divided by total number of data and multiplied by 100%) is reported in percent as percent below the upper limit, such as percent below 1 micrometer diameter or %-submicron, for example. The measured diameter (in μm) of an individual circular fibrous element is denoted as "$d_i$".

In the case that the fibrous elements have non-circular cross-sections, the measurement of the fibrous element diameter is determined as and set equal to the hydraulic diameter which is four times the cross-sectional area of the fibrous element divided by the perimeter of the cross-section of the fibrous element (outer perimeter in case of hollow fibrous elements). The number-average diameter, alternatively average diameter is calculated as:

$$d_{num} = \frac{\sum_{i=1}^{n} d_i}{n}$$

Particle Size Distribution Test Method

The particle size distribution test is conducted to determine characteristic sizes of solid additives, for example particles. It is conducted using ASTM D 502-89, "Standard Test Method for Particle Size of Soaps and Other Detergents", approved May 26, 1989, with a further specification for sieve sizes and sieve time used in the analysis. Following section 7, "Procedure using machine-sieving method," nest of clean dry sieves containing U.S. Standard (ASTM E 11) sieves #4 (4.75 mm), #6 (3.35 mm), #8 (2.36 mm), #12 (1.7 mm), #16 (1.18 mm), #20 (850 micrometer), #30 (600 micrometer), #40 (425 micrometer), #50 (300 micrometer), #70 (212 micrometer), #100 (150 micrometer), #170 (90 micrometer), #325 (44 micrometer) and pan is required to cover the range of particle sizes referenced herein. The prescribed Machine-Sieving Method is used with the above sieve nest. A suitable sieve-shaking machine can be obtained from W.S. Tyler Company, Ohio, U.S.A. The sieve-shaking test sample is approximately 100 grams and is shaken for 5 minutes.

The data are plotted on a semi-log plot with the micrometer size opening of each sieve plotted on the logarithmic abscissa and the cumulative mass percent finer (CMPF) is plotted on the linear ordinate. An example of the above data representation is given in ISO 9276-1:1998, "Representation of results of particle size analysis—Part 1: Graphical Representation", FIG. A.4. A characteristic particle size (Dx, x=10, 50, 90), for the purpose of this invention, is defined as the abscissa value at the point where the cumulative mass percent is equal to x percent, and is calculated by a straight-line interpolation between the data points directly above (a) and below (b) the x value using the following equation:

$Dx=10^{[Log(Da)-(Log(Da)-Log(Db))*(Qa-x \%)/(Qa-Qb)]}$ where Log is the base 10 logarithm, Qa and Qb are the cumulative mass percentile values of the measured data immediately above and below the $x^{th}$ percentile, respectively; and Da and Db are the micrometer sieve size values corresponding to these data.

Example Data and Calculations:

| sieve size (micrometer) | weight on sieve (g) | cumulative mass % finer (CMPF) |
| --- | --- | --- |
| 1700 | 0 | 100% |
| 1180 | 0.68 | 99.3% |
| 850 | 10.40 | 89.0% |
| 600 | 28.73 | 60.3% |
| 425 | 27.97 | 32.4% |
| 300 | 17.20 | 15.2% |
| 212 | 8.42 | 6.8% |
| 150 | 4.00 | 2.8% |
| Pan | 2.84 | 0.0% |

For D10 (x=10), the micrometer screen size where CMPF is immediately above 10% (Da) is 300 micrometer, the screen below (Db) is 212 micrometer. The cumulative mass immediately above 10% (Qa) is 15.2%, below (Qb) is 6.8%. D10=10^[Log(300)-(Log(300)-Log(212))*(15.2%-10%)/(15.2%-6.8%)]=242 micrometer.

For D90 (x=90), the micrometer screen size where CMPF is immediately above 90% (Da) is 1180 micrometer, the screen below (Db) is 850 micrometer. The cumulative mass immediately above 90% (Qa) is 99.3%, below (Qb) is 89.0%. D90=10^[Log(1180)-(Log(1180)-Log(850))*(99.3%-90%)/(99.3%-89.0%)]=878 micrometer.

For D50 (x=50), the micrometer screen size where CMPF is immediately above 50% (Da) is 600 micrometer, the screen below (Db) is 425 micrometer. The cumulative mass immediately above 50% (Qa) is 60.3%, below (Qb) is 32.4%. D50=10^[Log(600)-(Log(600)-Log(425))*(60.3%-50%)/(60.3%-32.4%)]=528 micrometer.

Weight Average Molecular Weight

The weight average molecular weight (Mw) of a material, such as a polymer, is determined by Gel Permeation Chromatography (GPC) using a mixed bed column. A high-performance liquid chromatograph (HPLC) having the following components: Millenium®, Model 600E pump, system controller and controller software Version 3.2, Model 717 Plus autosampler and CHM-009246 column heater, all manufactured by Waters Corporation of Milford, Mass., USA, is utilized. The column is a PL gel 20 m Mixed A column (gel molecular weight ranges from 1,000 g/mol to 40,000,000 g/mol) having a length of 600 mm and an internal diameter of 7.5 mm and the guard column is a PL gel 20 m, 50 mm length, 7.5 mm ID. The column temperature is 55° C. and the injection volume is 200 μL. The detector is a DAWN® Enhanced Optical System (EOS) including Astra® software, Version 4.73.04 detector software, manufactured by Wyatt Technology of Santa Barbara, Calif., USA, laser-light scattering detector with K5 cell and 690 nm laser. Gain on odd numbered detectors set at 101. Gain on even numbered detectors set to 20.9. Wyatt Technology's Optilab® differential refractometer set at 50° C. Gain set at 10. The mobile phase is HPLC grade dimethylsulfoxide with 0.1% w/v LiBr and the mobile phase flow rate is 1 mL/min, isocratic. The run time is 30 minutes.

A sample is prepared by dissolving the material in the mobile phase at nominally 3 mg of material/1 mL of mobile phase. The sample is capped and then stirred for about 5 minutes using a magnetic stirrer. The sample is then placed in an 85° C. convection oven for 60 minutes. The sample is then allowed to cool undisturbed to room temperature. The sample is then filtered through a 5 m Nylon membrane, type Spartan-25, manufactured by Schleicher & Schuell, of Keene, N.H., USA, into a 5 milliliter (mL) autosampler vial using a 5 mL syringe.

For each series of samples measured (3 or more samples of a material), a blank sample of solvent is injected onto the column. Then a check sample is prepared in a manner similar to that related to the samples described above. The check sample comprises 2 mg/mL of pullulan (Polymer Laboratories) having a weight average molecular weight of 47,300 g/mol. The check sample is analyzed prior to analyzing each set of samples. Tests on the blank sample, check sample, and material test samples are run in duplicate. The final run is a run of the blank sample. The light scattering detector and differential refractometer is run in accordance with the "Dawn EOS Light Scattering Instrument Hardware Manual" and "Optilab® DSP Interferometric Refractometer Hardware Manual," both manufactured by Wyatt Technology Corp., of Santa Barbara, Calif., USA, and both incorporated herein by reference.

The weight average molecular weight of the sample is calculated using the detector software. A dn/dc (differential change of refractive index with concentration) value of 0.066 is used. The baselines for laser light detectors and the refractive index detector are corrected to remove the contributions from the detector dark current and solvent scattering. If a laser light detector signal is saturated or shows excessive noise, it is not used in the calculation of the molecular mass. The regions for the molecular weight characterization are selected such that both the signals for the 900 detector for the laser-light scattering and refractive index are greater than 3 times their respective baseline noise levels. Typically, the high molecular weight side of the chromatogram is limited by the refractive index signal and the low molecular weight side is limited by the laser light signal.

The weight average molecular weight can be calculated using a "first order Zimm plot" as defined in the detector software. If the weight average molecular weight of the sample is greater than 1,000,000 g/mol, both the first and second order Zimm plots are calculated, and the result with the least error from a regression fit is used to calculate the molecular mass. The reported weight average molecular weight is the average of the two runs of the material test sample.

Dissolution Test Method
Protocol
(1) To a 100 g clear glass jar, add 75 g water and a 1" magnetic stir bar.
(2) Place jar onto a stir plate and begin agitation.
(3) Increase agitation speed until a vortex of circa 4 cm is obtained (Vortex height is obtained by measuring the vortex from base apex to vortex opening).
(4) Weigh 1 sample & record weight. Sample weight should be 0.40 grams (+/−0.05 grams).
(5) Simultaneously place sample into jar on stir plate and begin timer.
(6) Mix for 1 minute. Turn off stirring & remove jar from stir plate.
(7) Visually assess solution for undissolved material and clarity of resulting solution per the dissolution quality assessment scale as shown in Table 1 below.

TABLE 1

| Dissolution Quality Assessment Scale | |
|---|---|
| Rating | Solution Characteristics Post Mixing |
| 5 | Sample fully dissolved; no visible pieces of residual fiber in solution. |
| 4 | Sample almost fully dissolved; less than 5 residual fibers having a rough diameter of less than about 3 mm. |
| 3 | Sample partially dissolved; many pieces of residual fibers having a rough diameter of less than about 3 mm. |
| 2 | Sample poorly dissolved; large, undissolved fibers with a diameter larger than 3 mm, but less than 5 mm. |
| 1 | Sample not dissolved; large undissolved fibers with a diameter larger than 5 mm. |

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

The following water-soluble personal cleansing products Ex. 1-2 comprising water-soluble fibrous structure and coated with an oily composition and comparative products CEx. 1 as shown below were prepared.

Each example was used for removing a waterproof mascara commercially available as "Better Than Sex Waterproof Mascara" supplied by Too Faced and applied at the ocular region by one of the personal cleansing products below. Then the dissolution in water of each used product was assessed. The following observations were reported:

Compositions (% wt.)

| | | CEx. 1 | | Ex. 1 | | Ex. 2 | |
|---|---|---|---|---|---|---|---|
| | Components | % wt. based on the oily composition | % wt. based on the dry water-soluble fibrous structure basis | % wt. based on oily composition | % wt. based on the dry water-soluble fibrous structure basis | % wt. based on oily composition | % wt. based on the dry water-soluble fibrous structure basis |
| Fibrous Element-forming composition | Starch*[1] | | 99.1% | | 99.1% | | 99.1% |
| | Sulfosuccinate surfactant (process aid)*[2] | | 0.9% | | 0.9% | | 0.9% |
| Oily composition | Petrolatum*[3] | 100% | | — | | — | |
| | Capric/caprylic triglycerides*[4] | — | | 100% | | 60% | |
| | Isopropyl palmitate*[5] | — | | — | | 40% | |

|  | | CEx. 1 | | Ex. 1 | | Ex. 2 | |
|---|---|---|---|---|---|---|---|
| | Components | % wt. based on the oily composition | % wt. based on the dry water-soluble fibrous structure basis | % wt. based on oily composition | % wt. based on the dry water-soluble fibrous structure basis | % wt. based on oily composition | % wt. based on the dry water-soluble fibrous structure basis |
| Observations | Removal of the mascara | Left too many oil residues on the ocular region | | Mascara has been removed | | Mascara has been removed | |
| | Dissolution in water after usage | Not readily soluble | | Almost dissolved | | Fully dissolved | |

Definitions of Components
*[1]Ingredion AMIOCA starch
*[2]Aerosol AOT-70 from Cytec Industries, Inc.
*[3]petrolatum from Sonneborn, White Petrolatum
*[4]Capric/caprylic triglycerides from Croda, SP Crodamol GTCC MBAL LQ
*[5]Isopropyl palmitate from ALZO International, Wickenol 111

Hence, when the water-soluble personal cleansing product is coated with an oily composition, the oily composition can help to prevent water or moisture to be immediately absorb by the personal cleansing product.

With CEx. 1, the oily composition comprising petrolatum allowed dissolving the waterproof mascara residues, however, the personal cleansing product was not readily water-soluble after usage.

With Ex. 1, the oily composition comprising Capric/caprylic triglycerides allowed dissolving the waterproof mascara residues, and, the personal cleansing product was not satisfactory water-soluble after usage.

With Ex. 2, the oily composition comprising Capric/caprylic triglycerides and isopropyl palmitate in a weight ratio 60:40 allowed dissolving the waterproof mascara residues, and the personal cleansing product was fully water-soluble after usage.

The following water-soluble personal cleansing products Ex. 3-4 comprising a water-soluble fibrous structure and coated with a cleansing composition and comparative product CEx. 2 as shown below were prepared.

Each example was used for removing a waterproof mascara applied at the ocular region by one of the personal cleansing products below. Then, the dissolution in water of each used product was assessed. The following observations were reported:

Compositions (% wt.)

|  | | CEx. 2 | | Ex. 3 | | Ex. 4 | |
|---|---|---|---|---|---|---|---|
| | Components | % wt. based on the cleansing composition | % wt. based on the dry water-soluble fibrous structure basis | % wt. based on oily composition | % wt. based on the dry water-soluble fibrous structure basis | % wt. based on oily composition | % wt. based on the dry water-soluble fibrous structure basis |
| Fibrous Element-forming composition | Starch*[1] | | 99.1% | | 99.1% | | 99.1% |
| | Sulfosuccinate surfactant (process aid)*[2] | | 0.9% | | 0.9% | | 0.9% |
| Cleansing composition | Disodium cocoyl glutamate*[6] | — | | 35% | | 30% | |
| | Sodium lauroamphoacetate*[7] | — | | — | | 5% | |
| | Citric acid*[8] | — | | 1.5% | | 1.5% | |
| | Water | — | | qsp | | qsp | |
| Observations | Removal of the mascara | No removal | | Mascara has been removed | | Mascara has been removed | |
| | Dissolution in water after usage | Fully dissolved | | Fully dissolved | | Fully dissolved | |

Definitions of Components
*[1]Ingredion ® AMIOCA starch
*[2]Aerosol AOT-70 from Cytec ® Industries, Inc.
*[6]Disodium cocoyl glutamate, Eversoft ® UCS-50S from Sino Lion ™
*[7]Sodium lauroamphoacetate Miranol Ultra L-32 from Solvay ®
*[8]Citric acid from Archer Daniels Midland ® Company Hence, when the water-soluble personal cleansing product is coated with acleansing composition, the cleansing composition can help to prevent water or moisture to beimmediately absorb by the personal cleansing product.

With CEx. 2, the water-soluble personal cleansing product did not comprise any coating, thus no waterproof mascara could be removed. However, the personal cleansing product was readily water-soluble after usage.

With Ex. 3, the cleansing composition comprising as the surfactant disodium cocoyl glutamate allowed dissolving the waterproof mascara residues, and the personal cleansing product was fully water-soluble after usage.

With Ex. 4, the cleansing composition comprising as the surfactants, disodium cocoyl glutamate and sodium lauroamphoacetate allowed dissolving the waterproof mascara residues, and the personal cleansing product was fully water-soluble after usage.

Other Observations

When the personal cleansing product is made with polylactic acid instead of starch, the resulting personal cleansing product was compostable but not water-soluble.

Another benefit associated with the examples is that the water-soluble personal cleansing products are free of preservatives and perfumes. Any skin irritation typically generated due to the presence of preservative systems or perfumes is therefore prevented.

Also, the water-soluble personal cleansing products within the scope of the invention appear to be softer and readily pliable, i.e. enough flexible to be applied under the eye and at each corner of the ocular region of the facial skin.

Method of Preparation

The above water-soluble fibrous structures of CEx. 1, CEx. 2 and "Ex. 1" through "Ex. 4" were prepared by the following method:

First, a fibrous element-forming composition was prepared by adding water to a container under sufficient stirring, then adding the Ingredion AMIOCA starch and Aerosol AOT-70. The mixture was heated to about 75° C. for about 2-3 hours. Then, the resulting mixture was cooled to about ambient temperature.

Then, the fibrous element-forming composition was pumped into a spinning die with 6 rows of circular extrusion nozzles, spaced from one another at a pitch of about 1.524 mm. The pumping rate was 500 g/min. The nozzles had individual inner diameters of about 0.305 mm and individual outside diameters of about 0.813 mm. Each individual nozzle comprised a melt capillary encircled by an annular and divergently flared orifice (concentric attenuation fluid hole) to supply attenuation air to each individual melt capillary. The respective fibrous element-forming composition extruded through the extrusion nozzles (fibrous element-forming holes) was surrounded and attenuated by generally cylindrical, humidified air streams supplied through the orifices to produce a plurality of fibrous elements. The temperature of the attenuation air was 40° C. The embryonic plurality of fibrous elements were dried by a drying air stream having a temperature of 220° C. by an electrical resistance heater supplied through drying nozzles and discharged at an angle of about 90 relative to the general orientation of the embryonic fibrous elements being spun. The dried fibrous elementswerecollectedonabelttoformafibrousstructureresultinginapersonal cleansing product. Thepersonalcleansingproductwasinaformofawipecomprisingatopandbottom surface.

Then, the top surface of the personal cleansing product in a form of a wipe was coated by the respective oily composition or cleansing composition.

The following kits A and B were prepared. Each kit comprises as a first water-soluble personal cleansing product, Ex. 2 and as a second water-soluble personal cleansing product one of the following examples Ex. 5 or Ex. 6.

Compositions (% wt.)

| | | KIT A | | KIT B | |
|---|---|---|---|---|---|
| | | First water-soluble personal cleansing product | | | |
| | | Ex. 2 | | Ex. 2 | |
| | | Second water-soluble personal cleansing product | | | |
| | | Ex. 5 | | Ex. 6 | |
| | Components | % wt. based on the fibrous element forming-composition | % wt. based on the dry water-soluble fibrous structure basis | % wt. based on the fibrous element forming-composition | % wt. based on the dry water-soluble fibrous structure basis |
|---|---|---|---|---|---|
| Fibrous Element-forming composition | Water | 4.00% | — | 4.00% | — |
| | Polyvinyl alcohol (PVA420H)*9 | 15.40% | 16.0% | 15.35% | 16.0% |
| | Polyvinyl alcohol (PVA403H)*10 | 15.40% | 16.0% | 15.35% | 16.0% |
| | Sorbitol*11 | 17.59% | 18.3% | 17.54% | 18.3% |
| | Disodium cocoyl glutamate*6 | 35.19% | 36.7% | 30.25% | 31.5% |
| | Sodium lauroamphoacetate*7 | — | — | 5.48% | 5.7% |
| | Sodium chloride from surfactants | 11.10% | 11.6% | 10.71% | 11.1% |

-continued

| | KIT A | | KIT B | |
|---|---|---|---|---|
| | First water-soluble personal cleansing product | | | |
| | Ex. 2 | | Ex. 2 | |
| | Second water-soluble personal cleansing product | | | |
| | Ex. 5 | | Ex. 6 | |
| Components | % wt. based on the fibrous element forming-composition | % wt. based on the dry water-soluble fibrous structure basis | % wt. based on the fibrous element forming-composition | % wt. based on the dry water-soluble fibrous structure basis |
| Citric acid*[8] | 1.32% | 1.4% | 1.32% | 1.4% |
| PEG-45M (Polyox N60K) | — | — | — | — |
| Total | 100% | 100% | 100% | 100% |

Definitions of Components
*[9]Polyvinyl alcohol (PVA420H) having a weight average molecular weight of 120 000 g/mol from Kuraray ®
*[10]Polyvinyl alcohol (PVA403H) having a weight average molecular weight of 30 000 g/mol from Kuraray ®
*[11]Sorbitol from Sigma-Aldrich ®

Method of Preparation

The above second water-soluble fibrous structures of "Ex. 5" through "Ex. 6" were prepared by the following method:

First, a fibrous element-forming composition was prepared by adding water to a container under sufficient stirring, then adding the polyvinyl alcohol polymer(s). The mixture was heated to about 75° C. for about 2-3 hours. Then, the resulting mixture was cooled to about ambient temperature. Desired one or more active agents, namely the one or more surfactants were added amd mix until a homogeneous solution was obtained. Any other ingredients (sorbitol, citric acid) were subsequently added. The resulting mixture was stirred until a uniform mixture was obtained.

Then, the fibrous element-forming composition was pumped into a spinning die with 6 rows of circular extrusion nozzles, spaced from one another at a pitch of about 1.524 mm. The pumping rate was 500 g/min. The nozzles had individual inner diameters of about 0.305 mm and individual outside diameters of about 0.813 mm. Each individual nozzle comprised a melt capillary encircled by an annular and divergently flared orifice (concentric attenuation fluid hole) to supply attenuation air to each individual melt capillary. The respective fibrous element-forming composition extruded through the extrusion nozzles (fibrous element-forming holes) was surrounded and attenuated by generally cylindrical, humidified air streams supplied through the orifices to produce a plurality of fibrous elements. The temperature of the attenuation air was 40° C. The embryonic plurality of fibrous elements were dried by a drying air stream having a temperature of 220° C. by an electrical resistance heater supplied through drying nozzles and discharged at an angle of about 90 relative to the general orientation of the embryonic fibrous elements being spun. The dried fibrous elements were collected on a belt to form a fibrous structure resulting in a personal cleansing product.

Additional Examples/Combinations

A. A water-soluble personal cleansing product, preferably a water-soluble facial cleansing product, comprising a water-soluble fibrous structure; wherein the water-soluble fibrous structure comprises a plurality of fibrous elements; wherein the plurality of fibrous elements comprises:

one or more fibrous element-forming materials comprising one or more hydroxyl polymers comprising a natural starch and/or a modified starch;

wherein the plurality of fibrous elements is substantially free of surfactant;

wherein the water-soluble personal cleansing product comprises one or more surfaces, preferably a top surface and a bottom surface, wherein the one or more surfaces, preferably the top surface, are coated with an oily composition, wherein the oily composition comprises one or more oil ingredients.

B. The water-soluble personal cleansing product of paragraph A, wherein the one or more oil ingredients are selected from the group consisting of butter, C12-C18 alkyl triglycerides, caprylic/capric/lauric triglyceride, caprylic/capric/ linoleic triglyceride, caprylic/capric/stearic triglyceride, caprylic/capric triglyceride, cocoa butter, C10-C18 alkyl triglycerides, egg oil, soybean oil, epoxidized soybean oil, glyceryl triacetyl hydroxystearate, glyceryl triacetyl ricinoleate, glycosphingolipids, hydrogenated castor oil, hydrogenated castor oil laurate, hydrogenated coconut oil, hydrogenated C12-C18 alkyl triglycerides, hydrogenated fish oil, hydrogenated lard, hydrogenated menhaden oil, hydrogenated mink oil, hydrogenated orange roughy oil, hydrogenated shark liver oil, hydrogenated tallow, hydrogenated vegetable oil, lanolin and lanolin derivatives, lanolin alcohol, lard, lauric/palmitic/oleic triglyceride, lesquerella oil, maleated soybean oil, neatsfoot oil, oleic/linoleic triglyceride, oleic/palmitic/lauric/myristic/linoleic triglyceride, oleostearine, olive husk oil, omental lipids, pengawar djambi oil, pentadesma butter, phospholipids, shea butter, tallow, tribehenin, tricaprin, tricaprylin, triheptanoin, trihydroxymethoxystearin, trihydroxystearin, triisononanoin, triisostearin, trilaurin, trilinolein, trilinolenin, trimyristin, trioctanoin, triolein, tripalmitin, trisebacin, tristearin, triundecanoin, and mixtures thereof.

C. The water-soluble personal cleansing product of paragraph A, wherein the one or more oil ingredients comprise an ester selected from the group consisting of isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, and oleyl adipate, and mixtures thereof.

D. The water-soluble personal cleansing product of paragraph A, wherein the oily composition comprises a blend of two or more oil ingredients selected from the group consisting of butter, C12-C18 alkyl triglycerides, caprylic/capric/lauric triglyceride, caprylic/capric/linoleic triglyceride, caprylic/capric/stearic triglyceride, caprylic/capric triglyceride, cocoa butter, C10-C18 alkyl triglycerides, egg oil, soybean oil, epoxidized soybean oil, glyceryl triacetyl hydroxystearate, glyceryl triacetyl ricinoleate, glycosphingolipids, hydrogenated castor oil, hydrogenated castor oil laurate, hydrogenated coconut oil, hydrogenated C12-C18 alkyl triglycerides, hydrogenated fish oil, hydrogenated lard, hydrogenated menhaden oil, hydrogenated mink oil, hydrogenated orange roughy oil, hydrogenated shark liver oil, hydrogenated tallow, hydrogenated vegetable oil, lanolin and lanolin derivatives, lanolin alcohol, lard, lauric/palmitic/oleic triglyceride, lesquerella oil, maleated soybean oil, neatsfoot oil, oleic/linoleic triglyceride, oleic/palmitic/lauric/myristic/linoleic triglyceride, oleostearine, olive husk oil, omental lipids, pengawar djambi oil, pentadesma butter, phospholipids, shea butter, tallow, tribehenin, tricaprin, tricaprylin, triheptanoin, trihydroxymethoxystearin, trihydroxystearin, triisononanoin, triisostearin, trilaurin, trilinolein, trilinolenin, trimyristin, trioctanoin, triolein, tripalmitin, trisebacin, tristearin, triundecanoin, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, and oleyl adipate, and mixtures thereof.

E. The water-soluble personal cleansing product of paragraph A, wherein the oily composition comprises a blend of an oil ingredient and an ester,
wherein the oil ingredient is selected from the group consisting of caprylic/capric/lauric triglyceride, caprylic/capric/linoleic triglyceride, caprylic/capric/stearic triglyceride, caprylic/capric triglyceride, lauric/palmitic/oleic triglyceride, oleic/linoleic triglyceride, oleic/palmitic/lauric/myristic/linoleic triglyceride, soybean oil, and mixtures thereof;
wherein the ester is selected from the group consisting of isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, and oleyl adipate, and mixtures thereof; and wherein the blend of the oil ingredient and the ester comprises a weight ratio of the total level of the oil ingredient to the ester from 80:20 to 40:60, preferably from 70:30 to 45:55, more preferably from 60:40 to 50:50.

F. The water-soluble personal cleansing product of paragraph E, wherein the oily composition comprises a blend of caprylic/capric triglyceride and isopropyl palmitate with a weight ratio of the total level of caprylic/capric triglyceride to isopropyl palmitate is from 60:40 to 50:50.

G. A water-soluble personal cleansing product, preferably a water-soluble facial cleansing product, comprising a water-soluble fibrous structure;
wherein the water-soluble fibrous structure comprises a plurality of fibrous elements; wherein the plurality of fibrous elements comprises:
one or more fibrous element-forming materials comprising one or more hydroxyl polymers comprising a natural starch and/or a modified starch;
wherein the plurality of fibrous elements is substantially free of surfactant;
wherein the water-soluble personal cleansing product comprises one or more surfaces, preferably a top surface and a bottom surface, wherein the one or more surfaces, preferably the top surface, are coated with a cleansing composition comprising one or more surfactants; and
wherein the cleansing composition is substantially free of alkyl sulfate and alkyl ether sulfate type of surfactants.

H. The water-soluble personal cleansing product of paragraph G, wherein the one or more surfactants comprise at least one glutamate surfactant according to the general formula (I):

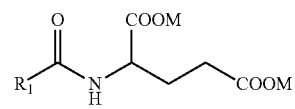

wherein $R_1$ is a saturated or unsaturated, straight or branched alkyl or alkenyl chain with from 5 to 20 carbon atoms, preferably with from 7 to 17 carbon atoms, more preferably with from 9 to 13 carbon atoms; and M is H, ammonium, triethanolammonium (TEA), sodium or potassium and mixtures thereof.

I. The water-soluble personal cleansing product of paragraph H, the at least one glutamate surfactant is selected from the group consisting of sodium cocoyl glutamate, disodium cocoyl glutamate, potassium cocoyl glutamate, dipotassium cocoyl glutamate, ammonium cocoyl glutamate, diammonium cocoyl glutamate, sodium lauroyl glutamate, disodium lauroyl glutamate, potassium lauroyl glutamate, dipotassium lauroyl glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallowoyl glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallowoyl glutamate, sodium cocoyl/palmoyl/sunfloweroyl glutamate, sodium hydrogenated tallowoyl glutamate, sodium olivoyl glutamate, disodium olivoyl glutamate, sodium palmoyl glutamate, disodium palmoyl glutamate, TEA-cocoyl glutamate, TEA-hydrogenated tallowoyl glutamate, TEA-lauroyl glutamate, and mixtures thereof; preferably wherein the at least one glutamate surfactant is selected from the group consisting of sodium cocoyl glutamate, disodium cocoyl glutamate, potassium cocoyl glutamate, dipotassium cocoyl glutamate, ammonium cocoyl glutamate, diammonium cocoyl glutamate, sodium lauroyl glutamate, disodium lauroyl glutamate, potassium lauroyl glutamate, dipotassium lauroyl glutamate, sodium capryloyl glutamate, disodium capryloyl glutamate, potassium capryloyl glutamate, dipotassium capryloyl glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, TEA-cocoyl glutamate, and mixtures thereof; more preferably wherein the at least one glutamate surfactant is selected from the group consisting of sodium cocoyl glutamate, disodium cocoyl glutamate, potassium cocoyl glutamate, dipotassium cocoyl glutamate, ammonium cocoyl glutamate, diammonium cocoyl glutamate, TEA-cocoyl glutamate, and mixtures thereof.

J. The water-soluble personal cleansing product of any of the preceding paragraphs G-I, wherein the one or more surfactants comprise a co-surfactant by weight of the composition, wherein the co-surfactant is selected from the group consisting of an anionic surfactant being not a glutamate surfactant, a non-ionic surfactant, an amphoteric surfactant, a zwitterionic surfactant, and mixtures thereof.

K. The water-soluble personal cleansing product of paragraph J, wherein the anionic surfactant being not a glutamate surfactant is selected from the group consisting of an isethionate surfactant, a sarcosinate surfactant, a glycinate surfactant, an alanitate surfactant, a sulfosuccinate surfactant, a sulfonate surfactant, a sulfoacetate surfactant, a glucose carboxylate surfactant, an alkyl ether carboxylate surfactant, a taurate surfactant, and mixtures thereof.

L. The water-soluble personal cleansing product of any of the preceding paragraphs G-K, wherein the one or more surfactants comprise at least one isethionate surfactant according to the general formula (II):

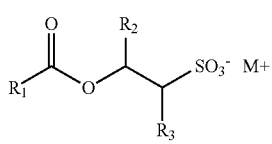

wherein $R_1$ is a saturated or unsaturated, straight or branched, alkyl or alkenyl chain with from 6 to 30 carbon atoms, preferably from 8 to 22 carbon atoms, more preferably from 9 to 18 carbon atoms, $R_2$ and $R_3$ are each independently H or $(C_1-C_4)$ alkyl, preferably wherein $(C_1-C_4)$ alkyl is methyl, and $M^+$ is an alkali metal, preferably lithium, sodium, potassium; or $M^+$ is an alkali-earth metal, preferably magnesium; or $M^+$ is an ammonium or a substituted ammonium cation.

M. The water-soluble personal cleansing product of paragraph L, wherein the at least one isethionate surfactant is selected from the group consisting of sodium lauroyl isethionate, sodium lauroyl methyl isethionate, sodium oleoyl isethionate, sodium oleoyl methyl isethionate, sodium stearoyl isethionate, sodium stearoyl methyl isethionate, sodium myristoyl isethionate, sodium myristoyl methyl isethionate, sodium palmitoyl isethionate, sodium palmitoyl methyl isethionate, sodium cocoyl isethionate, sodium cocoyl methyl isethionate, a blend of stearic acid and sodium cocoyl isethionate, ammonium cocoyl isethionate, ammonium cocoyl methyl isethionate, and mixtures thereof.

N. The water-soluble personal cleansing product of any of the preceding paragraphs G-M, wherein the one or more surfactants comprise at least an amphoteric or zwitterionic surfactant selected from the group consisting of cocamidopropyl betaine, lauramidopropyl betaine, coco-betaine, lauryl betaine, lauryl hydroxysultaine, cocamidopropyl hydroxysultaine, coco-hydroxysultaine, coco-sultaine, lauryl sultaine, sodium cocoamphoacetate, disodium cocoamphodiacetate, sodium lauroamphoacetate, disodium lauroamphodiacetate, lauramine oxide, and mixtures thereof.

O. The water-soluble personal cleansing product of any of the preceding paragraphs G-N, wherein the one or more surfactants comprise a non-ionic surfactant, wherein the non-ionic surfactant is selected from the group consisting alkyl polyglucoside, alkyl glycoside, acyl glucamide and mixtures thereof, preferably wherein the non-ionic surfactant is selected from the group consisting of decyl glucoside, cocoyl glucoside, lauroyl glucoside, and mixtures thereof.

P. The water-soluble personal cleansing product of any of the preceding paragraphs A-O, wherein the one or more hydroxyl polymers comprise a natural starch having a level of amylopectin greater than 75% by weight of starch.

Q. The water-soluble personal cleansing product of any of the preceding paragraphs A-P, wherein the natural starch is selected from the group consisting of corn starch, potato starch, sweet potato starch, wheat starch, sago palm starch, tapioca starch, rice starch, soybean starch, arrow root starch, amioca starch, bracken starch, lotus starch, waxy maize starch, high amylose corn starch, and mixtures thereof.

R. The water-soluble personal cleansing product of any of the preceding paragraphs A-Q, wherein the natural starch comprises a waxy maize starch having a weight average molecular weight of from 500,000 g/mol to 40,000,000 g/mol according to the weight average molecular weight test method.

S. The water-soluble personal cleansing product of any of the preceding paragraphs A-R, wherein the modified starch is selected from the group consisted of hydroxyethylated starch, hydroxypropylated starch, ethersuccinylated starch, acetylated starch, carbamate starch, and mixtures thereof.

T. The water-soluble personal cleansing product of any of the preceding paragraphs A-S, wherein the modified starch comprises hydroxyethylated starch having a weight average molecular weight of from 200,000 g/mol to 10,000,000 g/mol according to the weight average molecular weight test method.

U. The water-soluble personal cleansing product of any of the preceding paragraphs A-T, wherein the one or more hydroxyl polymers have a weight average molecular weight of from 10,000 g/mol to 40,000,000 g/mol, preferably from 100,000 g/mol to 10,000,000 g/mol, more preferably from 1,000,000 g/mol to 3,000,000 g/mol according to the weight average molecular weight test method.

V. The water-soluble personal cleansing product of any of the preceding paragraphs A-U, wherein the one or more hydroxyl polymers comprising a natural starch and/or a modified starch are not cross-linked.

W. The water-soluble personal cleansing product of any of the preceding paragraphs A-V, wherein the one or more fibrous element-forming materials further comprises one or more polymers selected from the group consisting of polyacrylamide, carboxyl modified polyacrylamide, polyacrylic acid, poly(hydroxyethyl acrylic acid), polymethacrylic acid and partial esters, polyvinyl alcohol, carboxymethyl cellulose, hydroxypropylmethyl cellulose, polyvinylpyrrolidone, polyamide, polyethylene oxide, and mixtures thereof.

X. The water-soluble personal cleansing product of any of the preceding paragraphs A-W, wherein the plurality of fibrous elements comprises one or more filaments and/or one or more fibers.

Y. The water-soluble personal cleansing product of any of the preceding paragraphs A-X, wherein the plurality of fibrous elements is meltblown and/or spunbond fibrous elements.

Z. The water-soluble personal cleansing product of any of the preceding paragraphs A-Y, wherein the plurality of fibrous elements comprises a plasticizer selected from the group consisting of glycerin, diglycerin, propylene glycol, ethylene glycol, butylene glycol, pentylene glycol, cyclohexane dimethanol, hexanediol, 2,2,4-trimethylpentane-1,3-diol, polyethylene glycol with a weight average molecular weight from 200 g/mol to 600 g/mol, pentaerythritol, sorbitol, manitol, lactitol, fructose, glucose, sucrose, maltose, lactose, high fructose corn syrup solids, dextrins, ascorbic acid, and mixtures thereof; preferably a plasticizer selected from the group consisting of glycerin, ethylene glycol, polyethylene glycol, propylene glycol, glycidol, urea, sorbitol, xylitol, maltitol, sugars, ethylene bisformamide, amino acids, and mixtures thereof.

AA. The water-soluble personal cleansing product of paragraph Z, wherein the total level of the plasticizer is from 1% to 40% by weight on a dry fibrous element basis and/or a dry water-soluble fibrous structure basis; preferably from 2% to 30% by weight on a dry fibrous element basis and/or a dry water-soluble fibrous structure basis; more preferably from 5% to 20% by weight on a dry fibrous element basis and/or a dry water-soluble fibrous structure basis.

BB. The water-soluble personal cleansing product of any of the preceding paragraphs A-AA, wherein the water-soluble personal cleansing product is in the form of a wipe, a pad, a facial cleansing wipe or facial cleansing pad for an adult or a baby, a bath tissue wipe, or a skin care substrate.

CC. The water-soluble personal cleansing product of any of the preceding paragraphs A-BB, wherein the water-soluble personal cleansing product is substantially free of preservatives.

DD. The water-soluble personal cleansing product of any of the preceding paragraphs A-CC, wherein the water-soluble personal cleansing product is substantially free of perfumes.

EE. Use of the water-soluble personal cleansing product of any of the preceding paragraphs A-DD for make-up removal from the skin, preferably for eye make-up removal.

FF. A kit for make-up removal from the skin, preferably for eye make-up removal, comprising:
i) a first water-soluble personal cleansing product comprising the water-soluble personal cleansing product of any of the preceding paragraphs A-DD; and
ii) a second water-soluble personal cleansing product, preferably a second water-soluble facial cleansing product comprising a water-soluble fibrous structure of the second water-soluble personal cleansing product;
wherein the water-soluble fibrous structure comprises a plurality of fibrous elements;
wherein the plurality of fibrous elements comprises:
one or more fibrous element-forming materials comprising one or more polyvinyl alcohol; and
one or more active agents present within the plurality of fibrous elements, wherein the one or more active agents comprise one or more surfactants, wherein the one or more surfactants comprise at least one glutamate surfactant according to the general formula (I):

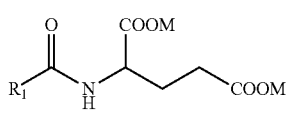

wherein $R_1$ is a saturated or unsaturated, straight or branched alkyl or alkenyl chain with from 5 to 20 carbon atoms, preferably with from 7 to 17 carbon atoms, more preferably with from 9 to 13 carbon atoms; and M is H, ammonium, triethanolammonium (TEA), sodium or potassium and mixtures thereof; and
wherein the water-soluble fibrous structure of the second water-soluble personal cleansing product is substantially free of alkyl sulfate and alkyl ether sulfate type of surfactants.

GG. A method for make-up removal from the skin, preferably for eye make-up removal, comprising the following steps, preferably in that order:
a) providing the water-soluble personal cleansing product as defined in any of the preceding paragraphs A-DD;
b) removing any make-up residues from the skin by applying the one or more surfaces, preferably the top surface, of the water-soluble personal cleansing product comprising the oily composition; optionally rinsing with water.

HH. The method for make-up removal from the skin of paragraph GG, comprising the following steps, preferably in that order:
c) providing a second water-soluble personal cleansing product, preferably a second water-soluble facial cleansing product, comprising a water-soluble fibrous structure of the second water-soluble personal cleansing product;
wherein the water-soluble fibrous structure comprises a plurality of fibrous elements;
wherein the plurality of fibrous elements comprises:
one or more fibrous element-forming materials comprising one or more polyvinyl alcohol; and
one or more active agents present within the plurality of fibrous elements, wherein the one or more active agents comprise one or more surfactants, wherein the one or more surfactants comprise at least one glutamate surfactant according to the general formula (I):

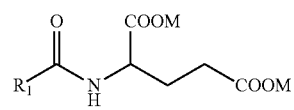

wherein $R_1$ is a saturated or unsaturated, straight or branched alkyl or alkenyl chain with from 5 to 20 carbon atoms, preferably with from 7 to 17 carbon atoms, more preferably with from 9 to 13 carbon atoms; and M is H, ammonium, triethanolammonium (TEA), sodium or potassium and mixtures thereof
d) wetting the second water-soluble personal cleansing product with water to obtain a cleansing solution;
e) shearing the cleansing solution to generate lathering, preferably by rotating a palm of a user's hand against the cleansing solution; lathering and applying the cleansing solution to the skin; and
f) rinsing with water.

II. A method of making a water-soluble personal cleansing product comprising a water-soluble fibrous structure as defined in any of the preceding paragraphs A-DD comprising the following steps, preferably in that order:
a) providing a fibrous element-forming composition, wherein the fibrous element-forming composition is an aqueous composition comprising one or more fibrous element-forming materials; and
b) spinning the fibrous element-forming composition into a plurality of fibrous elements forming a water-soluble fibrous structure comprising a plurality of fibrous elements, preferably a plurality of filament elements.

JJ. The method of making a water-soluble personal cleansing product of paragraph II, wherein spinning the fibrous element-forming composition into a plurality of fibrous elements is provided by meltblowing, spunbonding, electrospinning, and/or rotary spinning.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention

What is claimed is:

1. A personal cleansing product comprising:
   a. a fibrous structure comprising: a plurality of water-soluble fibrous elements having a length to average diameter ratio of at least about 10 and a basis weight of from about 1 g/m² to about 3000 g/m²; wherein the fibrous elements comprise:
      i. an uncrosslinked natural starch and/or an uncrosslinked modified starch;
      ii. optionally less than 1% surfactant;
   wherein the fibrous structure comprises at least one surface coated with an oily composition.

2. The personal cleansing product of claim 1, wherein the oily composition comprises one or more oil ingredients selected from the group consisting of butter, caprylic/capric/lauric triglyceride, caprylic/capric/linoleic triglyceride, caprylic/capric/stearic triglyceride, caprylic/capric triglyceride, cocoa butter, C10-C18 alkyl triglycerides, egg oil, soybean oil, epoxidized soybean oil, glyceryl triacetyl hydroxystearate, glyceryl triacetyl ricinoleate, glycosphingolipids, hydrogenated castor oil, hydrogenated castor oil laurate, hydrogenated coconut oil, hydrogenated C12-C18 alkyl triglycerides, hydrogenated fish oil, hydrogenated lard, hydrogenated menhaden oil, hydrogenated mink oil, hydrogenated orange roughy oil, hydrogenated shark liver oil, hydrogenated tallow, hydrogenated vegetable oil, lanolin and lanolin derivatives, lanolin alcohol, lard, lauric/palmitic/oleic triglyceride, lesquerella oil, maleated soybean oil, neatsfoot oil, oleic/linoleic triglyceride, oleic/palmitic/lauric/myristic/linoleic triglyceride, oleostearine, olive husk oil, omental lipids, pengawar djambi oil, pentadesma butter, phospholipids, shea butter, tallow, tribehenin, tricaprin, tricaprylin, triheptanoin, trihydroxymethoxystearin, triisononanoin, triisostearin, trilaurin, trilinolein, trilinolenin, trimyristin, trioctanoin, triolein, tripalmitin, trisebacin, tristearin, triundecanoin, or a combination thereof.

3. The personal cleansing product of claim 1, wherein the oily composition comprises an ester selected from the group consisting of isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, oleyl adipate, or a combination thereof.

4. The personal cleansing product of claim 1, wherein the oily composition comprises a blend of two or more oil ingredients selected from the group consisting of butter, caprylic/capric/lauric triglyceride, caprylic/capric/linoleic triglyceride, caprylic/capric/stearic triglyceride, caprylic/capric triglyceride, cocoa butter, C10-C18 alkyl triglycerides, egg oil, soybean oil, epoxidized soybean oil, glyceryl triacetyl hydroxystearate, glyceryl triacetyl ricinoleate, glycosphingolipids, hydrogenated castor oil, hydrogenated castor oil laurate, hydrogenated coconut oil, hydrogenated C12-C18 alkyl triglycerides, hydrogenated fish oil, hydrogenated lard, hydrogenated menhaden oil, hydrogenated mink oil, hydrogenated orange roughy oil, hydrogenated shark liver oil, hydrogenated tallow, hydrogenated vegetable oil, lanolin and lanolin derivatives, lanolin alcohol, lard, lauric/palmitic/oleic triglyceride, lesquerella oil, maleated soybean oil, neatsfoot oil, oleic/linoleic triglyceride, oleic/palmitic/lauric/myristic/linoleic triglyceride, oleostearine, olive husk oil, omental lipids, pengawar djambi oil, pentadesma butter, phospholipids, shea butter, tallow, tribehenin, tricaprin, tricaprylin, triheptanoin, trihydroxymethoxystearin, triisononanoin, triisostearin, trilaurin, trilinolein, trilinolenin, trimyristin, trioctanoin, triolein, tripalmitin, trisebacin, tristearin, triundecanoin, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, oleyl adipate, or a combination thereof.

5. The personal cleansing product of claim 1, wherein the oily composition comprises a blend of an oil ingredient and an ester selected from the group consisting of caprylic/capric/lauric triglyceride, caprylic/capric/linoleic triglyceride, caprylic/capric/stearic triglyceride, caprylic/capric triglyceride, lauric/palmitic/oleic triglyceride, oleic/linoleic triglyceride, oleic/palmitic/lauric/myristic/linoleic triglyceride, soybean oil, or a combination thereof;
   wherein the ester comprises isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, oleyl adipate, or a combination thereof; and
   wherein the blend of the oil ingredient and the ester comprises a weight ratio of the total level of the oil ingredient to the ester from about 80:20 to about 40:60.

6. The personal cleansing product of claim 5, wherein the oily composition comprises a blend of caprylic/capric triglyceride and isopropyl palmitate with a weight ratio of the total level of caprylic/capric triglyceride to isopropyl palmitate is from about 60:40 to about 50:50.

7. The personal cleansing product according to claim 1, wherein the plurality of fibrous elements are free of surfactant.

8. The personal cleansing product of claim 1, wherein the fibrous elements comprise an uncrosslinked natural starch having a level of amylopectin greater than about 75% by weight of starch.

9. The personal cleansing product of claim 1, wherein the uncrosslinked natural starch is selected from the group consisting of corn starch, potato starch, sweet potato starch, wheat starch, sago palm starch, tapioca starch, rice starch, soybean starch, arrow root starch, amioca starch, bracken starch, lotus starch, waxy maize starch, high amylose corn starch, or a combination thereof.

10. The personal cleansing product of claim 1, wherein the uncrosslinked natural starch comprises a waxy maize starch having a weight average molecular weight of from about 500,000 g/mol to about 40,000,000 g/mol according to the weight average molecular weight test method.

11. The personal cleansing product of claim 1, wherein the uncrosslinked modified starch selected from the group consisting of hydroxyethylated starch, hydroxypropylated starch, ethersuccinylated starch, acetylated starch, carbamate starch, or a combination thereof.

12. The personal cleansing product of claim 11, wherein the modified starch comprises hydroxyethylated starch having a weight average molecular weight of from about 200,000 g/mol to about 10,000,000 g/mol according to the weight average molecular weight test method.

13. The personal cleansing product of claim 1, wherein the one or more fibrous element-forming materials have a weight average molecular weight of from about 10,000 g/mol to about 40,000,000 g/mol according to the weight average molecular weight test method.

14. The personal cleansing product of claim 1, wherein the fibrous elements further comprise one or more polymers selected from the group consisting of polyacrylamide, carboxyl modified polyacrylamide, polyacrylic acid, poly(hydroxyethyl acrylic acid), polymethacrylic acid, polyvinyl alcohol, carboxymethyl cellulose, hydroxypropylmethyl cellulose, polyvinylpyrrolidone, polyamide, polyethylene oxide, or a combination thereof.

15. The personal cleansing product of claim 1, wherein the fibrous elements are meltblown fibrous elements.

16. The personal cleansing product of claim 1, wherein the product is in the form of a wipe, a pad, a facial cleansing wipe or facial cleansing pad, a bath tissue wipe, and/or a skin care substrate.

17. The personal cleansing product of claim 1, wherein the personal cleansing product comprises less than 0.3% of preservatives.

18. The personal cleansing product of claim 1, wherein the personal cleansing product comprises less than 0.3% of perfumes.

19. A kit for make-up removal from Ma a skin comprising:
   i) the personal cleansing product of claim 1; and
   ii) a second personal cleansing product comprising a second fibrous structure;
   wherein the second fibrous structure comprises a plurality of water-soluble fibrous elements comprising:
   a polyvinyl alcohol and
   a glutamate surfactant according to the general formula (I):

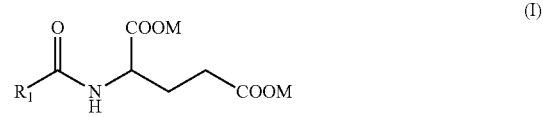

wherein $R_1$ is a saturated or unsaturated, straight or branched alkyl or alkenyl chain with from 5 to 20 carbon atoms; and M is H, ammonium, triethanolammonium, sodium or potassium and mixtures thereof.

20. A method for make-up removal from Ma a skin comprising the following steps, in that order:
   a) providing the personal cleansing product according to claim 1;
   b) removing any make-up residues from the skin by applying the surface of the personal cleansing product that is coated with the oily composition to the skin.

21. The personal cleansing product of claim 1, wherein the fibrous elements comprise fibers having a length of less than 5.08 cm.

22. The personal cleansing product of claim 1, wherein the fibrous elements comprise filaments having a length of greater than or equal to 5.08 cm.

* * * * *